United States Patent [19]

Darkwa et al.

[11] Patent Number: 5,679,327
[45] Date of Patent: Oct. 21, 1997

[54] HAIR STRAIGHTENING EMULSION

[75] Inventors: Adu Gyamfi Darkwa, Chicago; Apolonio L. Villanueva, III, Northbrook, both of Ill.

[73] Assignee: Johnson Products Co., Inc., Chicago, Ill.

[21] Appl. No.: 519,287

[22] Filed: Aug. 25, 1995

[51] Int. Cl.$^6$ .............................. A61K 7/09; A61K 7/07
[52] U.S. Cl. ...................... 424/70.4; 424/70.2; 132/204
[58] Field of Search ............................ 424/70.2, 70.41; 132/204

[56] References Cited

U.S. PATENT DOCUMENTS

| | | |
|---|---|---|
| 3,288,770 | 11/1966 | Butler . |
| 3,412,019 | 11/1968 | Hoover et al. . |
| 4,175,572 | 11/1979 | Hsiung et al. . |
| 4,237,910 | 12/1980 | Khahil et al. . |
| 4,304,244 | 12/1981 | de La Guardia . |
| 4,390,033 | 6/1983 | Khalil et al. . |
| 4,416,296 | 11/1983 | Meyers . |
| 4,524,787 | 6/1985 | Khalil et al. . |
| 4,605,018 | 8/1986 | de La Guardia et al. . |
| 4,772,462 | 9/1988 | Boothe et al. . |
| 4,950,485 | 8/1990 | Akhtar et al. . |
| 5,068,101 | 11/1991 | Akhtar et al. . |
| 5,077,042 | 12/1991 | Darkwa et al. . |
| 5,171,565 | 12/1992 | Akhtar et al. . |
| 5,275,809 | 1/1994 | Chen et al. . |
| 5,304,370 | 4/1994 | Hawkins et al. . |
| 5,376,364 | 12/1994 | Darkwa et al. . |

OTHER PUBLICATIONS

Holtzclaw, Jr. et al., *General Chemistry*, (Seventh Ed.), D. C. Heath & Co., p. 189, (1984).

Brown et al., *Chemistry The Central Science*, (Second Ed.), Prenctice–Hall, Inc., pp.360 and 450–451, (1981).

March, *Advanced Organic Chemistry*, (Fourth Ed.), John Wiley & Sons, Inc., p. 248, (1992).

Garcia et al., "Letter to the Editor," *J. Soc. Cosm. Chem.*, 41, 149–154, (1990).

Elliot, "Use of a Laboratory Model to Evaluate the Factors Influencing the Performance of Depilatories," *J. Soc. Cosm. Chem.*, 25, 367–377, (1974).

Crawford, R. J. & Robbins, C. R., "A Replacement of Rubine Dye for Detecting Cationics on Keratin," *J. Soc. Cosm. Chem.*, 31, 273–278, (1980).

deNavarre, Maison, G. (Ed.), *The Chemistry and Manufacture of Cosmetics*, 2nd edition, Continental Press, pp. 1155–1160, (1975).

Harris, Ronald T., "Hair Relaxing," *Cosmetics & Toiletries*, 94, 51–56 (1979).

Gesslein, B. W. et al., "Behenyl and Isostearyl Quaternaries," *Soap/Cosmetics/Chemical Specialties*, 66, pp. 36, 38, 41,44 & 104, (1990).

Balsam, M. S. and Sagarin, Edward, *Cosmetics Science and Technology*, 2nd edition, John Wiley & Sons, Inc. pp. 251, 264–267 & 277, (1972).

*Crodata: Incroguat Behenyl TMS*, Croda, Inc. (publication date unknown).

*Primary Examiner*—Sallie M. Gardner
*Attorney, Agent, or Firm*—Kirschstein, Ottinger, Israel & Schiffmiller, P.C.

[57] ABSTRACT

An improved highly alkaline hair straightening emulsion and a two component system for preparing the emulsion are provided. The emulsion employs a combination of strong nitrogenous organic base and alkali metal hydroxide in the presence of an alkaline earth metal cation. Neither the amount of the alkali metal hydroxide nor the amount of organic base present in the emulsion is sufficient by itself to effectively permanently straighten naturally curly hair. Alkaline earth metal hydroxides are characteristically ineffective as permanent hair straighteners. However, surprisingly, the combination is effective for achieving permanent straightening of hair within a treatment time of not more than about 30 minutes. In use, the emulsion also substantially avoids scalp skin irritation. Also, hair discoloration and hair breakage are minimized.

26 Claims, No Drawings

HAIR STRAIGHTENING EMULSION

TECHNICAL FIELD

This invention relates to improved highly alkaline emulsions that permanently straighten naturally curly hair and to a two-component system for preparing same.

BACKGROUND ART

Highly-alkaline, permanent hair-straightening, oil-in-water emulsion compositions are well known in the hair care art and are commonly used in salons and in the home. These compositions are usually highly-alkaline so that their pH is typically above about 11.5 and below about 14. They contain an effective hair-straightening amount of water-soluble strong chemical base.

As used herein, a term such as "permanent hair straightening," "permanently straighten hair" and equivalents thereof denotes the permanent removal of curliness in treated naturally curly hair that is chemically achieved and that produces a visibly straight hair configuration that does not revert to its previously untreated naturally curly state.

It is understood in the art that permanent hair straightening is achieved by a combination of the action of a strong chemical base and physical tensional forces (i.e., combing, tension, and smoothing among other things). It is also understood that one of the principle characteristics of effective and substantially complete permanent hair straightening is the inducement of supercontraction and radial swelling of the individual hair fibers which changes the fiber geometry.

The term "strong chemical base" as used herein denotes both physiologically tolerable, water-soluble, non-volatile inorganic alkalies (caustic bases) and relatively strong organic nitrogenous bases that are capable of relaxing the hair. Examples of such caustic bases include alkali metal hydroxides, such as sodium hydroxide (lye), potassium hydroxide, or lithium hydroxide, and also alkaline earth metal hydroxides, such as calcium hydroxide, barium hydroxide and strontium hydroxide, as well as oxides thereof that are capable of forming hydroxides in water and the like. Examples of such relatively strong organic bases conventionally include guanidine, hydrated guanidine (guanidine hydroxide, guanidinium hydroxide or the like) or quaternary ammonium hydroxides, and the like.

In the past, a skin-protective oleaginous material (or equivalent) was commonly applied to the scalp of the user before the user's curly hair was contacted with a highly alkaline hair relaxing or hair straightening composition. However, to avoid such a separate scalp protective application step in a hair relaxing or hair straightening process sequence, it has become commonplace to formulate the highly alkaline hair straightening composition as an oil-in-water emulsion that contains the skin-protective oleaginous material emulsified in the oil phase. Such an emulsion can be applied directly to the user's scalp hair and upon contact provides an immediate protective oleaginous material coating over the user's scalp skin. The use of a separately and preliminarily applied skin-protective material is thereby avoided.

Alkaline earth metal hydroxides are strong chemical bases. However, characteristically such hydroxides are not functional for use as permanent hair straighteners when used by themselves.

In prior hair straightening emulsions, caustic inorganic bases and relatively strong nitrogenous organic bases have each been separately incorporated in amounts at least sufficient for permanently straightening hair. For permanent hair straightening, an alkali metal hydroxide is, when used by itself in a hair straightening emulsion as the sole strong chemical base, generally employed at a concentration in the range of about 2 to about 4 weight percent calculated as hydroxide on a total emulsion weight basis or even higher. The alkali metal hydroxide of preference for most commercial hair straightening emulsions is sodium hydroxide. Lithium hydroxide is also used commercially, but to a lesser extent than sodium hydroxide, because it is generally more expensive and less readily available. In most commercial lithium hydroxide hair straightening, some calcium hydroxide is usually also included for buffering or for augmenting the pH at a molar ratio of lithium hydroxide to calcium hydroxide of above about 2:1. An alkali metal hydroxide such as sodium hydroxide and lithium hydroxide when used in such a hair straightening emulsion provides rapid, permanent straightening of the hair, but can cause skin irritation when the emulsion is in contact with the hair, scalp and the adjacent hair line skin.

For permanent hair straightening, a water-soluble nitrogenous organic base is, when used by itself in a hair straightening emulsion as the sole strong chemical base, generally employed at a concentration in the range of above about 2.5 weight percent calculated as free organic base on a total emulsion weight basis. The nitrogenous organic base of preference for most commercial hair straightening emulsions is guanidine or a hydrated guanidine (i.e., guanidine hydroxide, guanidinium hydroxide and the like) and mixtures thereof. Guanidine and hydrated guanidine are characteristically not stable for long periods in aqueous solution and so must be prepared fresh just before using. Consequently, conventional hair straightening emulsions employing guanidine or hydrated guanidine are usually supplied commercially as two-component kits. The two components are admixed together before use to form the hair straightening emulsion.

In commercial hair straightening systems incorporating such a nitrogenous organic base, usually one component of such a two-component kit comprises a saturated (about 28%) aqueous solution of guanidine carbonate and is commonly called the "activator component." The second component of such a kit usually comprises about 4 to about 10 weight percent of dissolved aqueous calcium hydroxide together with emulsified lipophilic oleaginous material and is commonly called the "cream" or "emulsion cream component." The molar ratio of guanidine carbonate to calcium hydroxide in the resulting mixture of activator component with emulsion cream component determines the amount of guanidine or hydrated guanidine that is produced in situ in the hair straightening emulsion. On prolonged standing, the guanidine or guanidine hydrate degrades, and the hair straightening emulsion product develops some odor of ammonia. Preferably, such emulsion product is applied to the user's hair within several hours of its formation. A water-soluble nitrogenous organic base such as guanidine and hydrated guanidine when used in such an emulsion product provides rapid permanent straightening of the hair, but can cause scalp skin irritation when the emulsion product is in contact with the hair and the adjacent scalp or hairline skin.

In the case of either one of such types of permanent hair straightening emulsions (that is, emulsions incorporating an alkali metal hydroxide and emulsions incorporating a nitrogenous base), as the active concentration of the strong chemical base which is necessary to achieve permanent hair straightening increases, proportionately less physical tensional force and less hair contact time is required to achieve substantially complete permanent hair straightening. Conversely, as the active concentration of the strong chemical base is decreased, proportionately more prolonged hair contact time of the hair with the emulsion product, and more physical tensional force, is required to effect substantially complete permanent hair straightening.

Perhaps because of their respective associated highly alkaline pH (the usual range being as above-indicated), either one of such prior art types of permanent hair straightening emulsions can cause problems. One problem is that skin irritation can result, particularly when the prior art hair straightening emulsion is allowed to remain in contact with the user's hair or skin for more than an acceptable time period. Another problem is that the user's hair can become structurally weakened during treatment so that excessive hair breakage in the resulting straightened hair results. Still another problem is that the natural color or tint of the user's hair can be altered. For example, if the user's hair is initially naturally gray in color, treatment can result in a visible yellowing of the hair. Such discoloration is undesirable. For example, a yellow tinge on gray hair is particularly undesirable because the white fibers in gray hair normally have a desirable natural bright tone which gives the hair highlights, whereas, when yellowed, this same hair looks dull, drab and lacks luster.

Permanent hair straightening should be achieved as quickly as possible to minimize skin irritation, hair damage, and/or hair discoloration from exposure to alkali. For persons having a "fine" type of hair, this can be generally readily achieved. However, for persons having "normal" and especially "coarse to resistant" hair, generally longer treatment (contact) times or greater concentrations of alkaline material or both are needed to effect permanent hair straightening. It is generally recognized in the hair straightening art that prolonged exposure (contact) of hair to the highly alkaline conditions required for permanent hair straightening increases the possibilities of irritating the scalp and hair line skin, of weakening the strength of the treated hair, and of hair discoloration. Thus, even though the extent of permanent hair straightening tend to improve in direct proportion to increased alkalinity and treatment (contact) time, so does the advent or likelihood of these adverse, undesired problems. To avoid or minimize such problems, it is common to limit the treatment time (that is, the time of contact between the emulsion and the user's scalp and hair) to a period that is not longer than about 30 minutes as is known to those familiar with the art.

Even with a short treatment time, the treated (contacted) hair may exhibit, after washing, optional setting, and drying, an undesirable rough or harsh texture or feel. Also, the treated hair may be difficult to comb without breakage. To overcome or reduce this type of problem, it is common to incorporate a hair conditioning agent into the hair straightening emulsion so that the treated hair has a better feel or hand thereafter. The conditioning agent can be present in the hair straightening cream emulsion, in the activator or in both. However, the conditioning agent may not reduce or overcome such rough hair texture or feel when the cause is the high alkalinity exposure (contact) needed for a hair straightening emulsion to achieve permanent hair straightening.

Substantial efforts have been made to achieve a hair straightening emulsion which not only provides permanent hair straightening in an acceptable maximum allowable treatment time of not more than about 30 minutes, but also concurrently reduces, minimizes or even eliminates skin irritation.

For example, to achieve permanent hair straightening particularly of coarse to resistant hair, within the indicated maximum treatment time, the amount of calcium hydroxide in the cream emulsion component should preferably be relatively high, (i.e., between about 4 and about 10 weight percent as above-indicated), and the activator component should preferably be a substantially saturated solution, (i.e., about 28 weight percent as above-indicated), of guanidine carbonate. Thereby, the amount of strong organic free base released in situ in the hair straightening emulsion when the cream emulsion component and the activator component are mixed together is maximized. However, these respective amounts of the precursor chemicals can present formulation and kit product shelf stability problems. Also, maximizing the amount of strong organic free base that is present in a hair straightening emulsion product made from the kit components may add to the chance of causing skin (including scalp) irritation during the treatment (contact) time period.

Moreover, merely reducing in a hair straightening emulsion the concentration and high alkalinity level of either its alkali metal hydroxide or its strong organic base only results in an emulsion which is incapable of achieving substantially complete permanent hair straightening in the required maximum treatment time. The term "substantially complete" as used herein in reference to permanent hair straightening means the substantially complete removal of the curliness of naturally curly previously untreated hair.

So far as now known, no one has previously succeeded in solving the problem of achieving with a highly alkaline emulsion substantially complete permanent hair straightening in the maximum treatment time while using only relatively low levels of strong chemical base and, preferably, while concurrently reducing the level of, or the probability of, skin (including scalp) irritation.

There is a substantial and long felt need in the art for an improved emulsion which employs relatively low levels of strong chemical base and which can achieve substantially complete permanent hair straightening of naturally curly, previously untreated hair within a hair contact time period of not more than about 30 minutes. Preferably such improved emulsion also demonstrates reduced skin irritation. The present invention provides such an emulsion.

SUMMARY OF THE INVENTION

This invention relates to a new and improved highly alkaline emulsion for permanently straightening previously untreated naturally curly hair on the scalp of a user through direct contact of the emulsion with the hair.

Substantially complete permanent hair straightening is achievable in a minimum acceptable contact time period with the emulsion product. The emulsion product achieves treated hair with minimal skin irritation, minimal hair breakage and minimal hair discoloration problems.

The invention also relates to an improved two-component hair straightener emulsion preparation kit comprised of an activator component and a cream emulsion component which permits one to freshly prepare the emulsion product of this invention immediately before use by admixing the two kit components together. The two component kit involves novel compositions that eliminate prior art shelf stability problems.

The hair straightening emulsion products of the invention employ a combination of three different types of dissolved, water-soluble strong chemical bases. One type is a nitrogenous organic base, a second type is an alkali metal hydroxide, and a third type is an alkaline earth metal hydroxide.

The respective quantity of each such strong chemical base that is present in a hair straightening emulsion of this invention is insufficient or inoperable for the purpose of producing substantially complete permanent hair relaxation when each said base is separately used as the sole strong chemical base in the emulsion within a hair contact time period of about 30 minutes. However, surprisingly and unexpectedly, when each such strong chemical base is used in combination in a hair straightening emulsion product of this invention as disclosed herein, substantially complete permanent hair straightening is achieved within a total hair contact time period of not longer than about 30 minutes without the disadvantages above-indicated. The combination of nitrogenous base, alkali metal hydroxide and alkaline earth metal hydroxide that is employed in the emulsions products of this invention is believed to be synergistic in effect.

The hair straightening emulsion products of this invention incorporate lipophilic oleaginous material and emulsifiers both generally being as known to the prior art. This incorporation is desirable because it enables use of conventional formulating and manufacturing techniques.

The hair straightening emulsion preparation kits of this invention permit one to prepare freshly and in situ the nitrogenous organic base in the presence of the alkali metal hydroxide and the alkaline earth metal hydroxide.

The hair straightening emulsion products of this invention are particularly effective when they contain certain types of hair conditioners. Particularly preferred hair conditioners for incorporation into such preferred emulsion products are the non-polymeric long chain ($C_{22}$) quaternary ammonium compounds which are classified as behenyltrimonium salts, such as behenyl trimethyl ammonium methosulfate, referred to for convenience as BTMS, and behenyl trimethyl ammonium chloride, referred to for convenience as BTMC. Also preferred as hair conditioners are quaternary nitrogen-containing polymers which are homopolymers, copolymers and terpolymers having a polydimethyldiallylammonium chloride (DMDAAC) moiety. Particularly preferred are the homopolymer of polydimethyldiallylammonium chloride (polyDMADAAC) and copolymers thereof containing DMAAC groups and the polyDMDAAC that is commonly known as POLYQUATERNIUM-6.

A presently particularly preferred hair straightening emulsion product of this invention is prepared from a preparation kit wherein the cream emulsion component employs, in combination, calcium hydroxide, lithium hydroxide, BTMS and POLYQUATERNIUM-6 and the activator component employs guanidine carbonate. Such a preferred emulsion product achieves hair straightening that is substantially equivalent to that achieved with conventional prior art no-lye type hair straightener emulsions which contain about twice the amount of the starting amounts of calcium hydroxide and guanidine carbonate. The use of relatively high concentrations of alkali metal hydroxide such as are known to cause problems with hair weakening and scalp and skin irritation is avoided altogether. In addition, the inventive emulsion product exhibits the characteristic low skin irritation property that is associated with conventional hair straighteners which employ only guanidine material as the strong chemical base. Moreover, this low skin irritation feature is achieved even though alkali metal hydroxide is also present.

Preferred cream emulsion components of the emulsion preparation kits provided by the present invention are prepared as phase-stable, oil-in-water emulsions.

The hair straightening emulsions of this invention apparently are no more weakening to the user's hair than prior art hair straighteners that are highly alkaline. Also, the inventive emulsion products are effective permanent hair straighteners yet they are substantially non-yellowing to natural gray hair. Additionally, unlike conventional no-lye type hair straightener emulsion products, the hair straightener emulsions of this invention particularly as prepared with the preferred emulsion cream components of this invention do not develop on standing an objectionable odor of ammonia (as the nitrogenous base undergoes its characteristic degradation).

The present invention provides a class of new and very useful cream emulsion components that are useful in the practice of making and using the inventive emulsions of this invention.

The present invention also provides new and useful methods of making new and improved highly alkaline hair straightening emulsions as well as new and useful methods of using new and improved highly alkaline hair straightening emulsions.

Other and further advantages and benefits associated with the hair straightening emulsions of this invention and their two component preparation kits will be apparent to those skilled in the art from the description, examples and claims which follow.

DETAILED DESCRIPTION OF THE INVENTION

In an emulsion product of this invention, the water-soluble nitrogenous organic base is present in an amount that is less than about 2 weight percent calculated as free organic base and based on total weight of the emulsion product. This amount is generally insufficient to produce substantially complete permanent hair straightening in a hair contact time period of about 30 minutes when the nitrogenous organic base is used as the sole strong chemical base in the emulsion.

The nitrogenous organic base is characterized by having:
(1) a $pK_a$ value of at least about 12, and
(2) in its molecular structure a carbon atom that is:
   doubly bonded to a first nitrogen atom,
   singly bonded to a second nitrogen atom, and also,
   singly bonded to either another carbon atom or to a third nitrogen atom.

Such organic base is selected from the group consisting of guanidines and acetamidines.

Also in an emulsion product of this invention, the water-soluble alkali metal hydroxide that is present is in an amount that is less than about 1 weight percent calculated as hydroxide and based on total weight of the emulsion product. This amount is generally insufficient to produce substantially complete permanent hair straightening in a hair contact time period of about 30 minutes when the alkali metal hydroxide is used as the sole strong chemical base in the emulsion.

Further initially present in an emulsion product of this invention is an alkaline earth metal hydroxide. As above-indicated, alkaline earth metal hydroxide is generally ineffective as a permanent hair straightener when used by itself as the sole strong chemical base in an emulsion.

Further present in emulsion components are both a lipophilic oleaginous material that is emulsified in the oil phase in said emulsion, and at least one emulsifier selected from the group consisting of lipophilic emulsifiers, hydrophilic emulsifiers and mixtures thereof.

In an emulsion product, the nitrogenous organic base is preferably produced in situ through hydrolysis of a dissolved, water-soluble salt of the nitrogenous organic base. The nitrogenous organic base salt is characterized by being hydrolysed in water at 25° C., ambient pressure, having a pH value that is about equal to a $pK_a$ value of at least about 12, and having a salt anion which forms, with an alkali earth metal cation, a substantially water-insoluble alkaline earth metal salt.

Preferably, the nitrogenous organic base is produced in situ in the presence of a dissolved water-soluble alkaline earth metal hydroxide. Thus, as produced, characteristically, there is also present produced in situ a substantially water-insoluble dispersed alkaline earth metal salt having an anion that is derived from the anion of the water-soluble salt of the nitrogenous organic base. The substantially water-insoluble alkaline earth metal salt preferably is dispersed in finely divided form in the emulsion.

A hair straightening emulsion product has a pH that is in the range of about 11.5 to about 14. This emulsion product particularly as prepared by admixing an activator component with a cream emulsion component contains initially alkaline earth metal hydroxide plus respective amounts of each of the organic base and the alkali metal hydroxide such that the combination comprises at least two strong chemical bases. An emulsion product is as those skilled in the art will appreciate a complex mixture and the exact chemical composition thereof is unknown or uncertain at any given time. For example, it is not now known if, after mixing of an activator component with a cream emulsion component to form an emulsion product, the alkaline earth metal hydroxide remains present or has been converted at least in part to a water-insoluble salt of the alkaline earth metal. However, as the data presented in the examples below indicates, at least two strong chemical bases (the nitrogenous organic base, and the alkali metal hydroxide) are necessary in combination with alkaline earth metal cations in an emulsion product for the purposes of the present invention. Those skilled in the art will appreciate that various preparation and mixing procedures can be used to prepare an emulsion product.

An emulsion product produces a substantially complete permanent straightening of the user's initially naturally hair when in contact therewith for a time period that is not longer than about 30 minutes, preferably less than about 25 minutes and more preferably less than about 20 minutes. The user's hair can be classified as fine, normal or coarse to resistant.

An emulsion product is further characterized by being substantially non-irritating to a user's scalp and hairline skin during the contact time of not more than about 30 minutes.

Preferably in a hair straightener emulsion product of the invention (based upon the total weight of the activator component and the cream emulsion component used in forming the emulsion product):

(a) the quantity of the nitrogenous organic base that is present in the emulsion product ranges from about 0.9 to about 2 weight percent calculated as free organic base, (b) the quantity of the alkali metal hydroxide that is present in the emulsion product ranges from about 0.5 to about 1 weight percent calculated as hydroxide, and (c) the quantity of the alkaline earth metal hydroxide initially present ranges from about 1.5 to about 3 weight percent calculated as hydroxide.

Preferably in an emulsion product, the alkaline earth metal cation comprises calcium.

Preferably in an emulsion product, the anion of the nitrogenous organic base salt is selected from the group consisting of carbonate, sulfate, sulfite, phosphite, fluoride, oxalate, tartrate, laurate, stearate, alginate and mixtures thereof.

When in an emulsion product, the nitrogenous organic base is a guanidine-type base (as now preferred), the base is preferably guanidine, hydrated guanidine, guanidine substituted with 1 through 5 substituents selected from the group consisting of lower alkyl, carboxy lower alkyl, hydroxy lower alkyl, amino, lower alkyl substituted amino groups, and mixtures thereof. Preferably such a base comprises guanidine, hydrated guanidine and mixtures thereof.

When in an emulsion product, the nitrogenous organic base is an acetamidine-type base, the base is selected from the group consisting of acetamidine, acetamidine substituted on the carbon atom with a substituent selected from the group consisting of lower alkyl, amino, lower alkyl substituted amino groups and mixtures thereof. Preferably, such a base comprises acetamidine.

Preferably in an emulsion product, the alkali metal is lithium, sodium or potassium and more preferably the alkali metal comprises lithium.

Preferably in an emulsion product on a 100 weight percent total emulsion product basis the quantity of lipophilic oleaginous material is in the range of about 5 to about 60 weight percent, the quantity of emulsifier is in the range of about 0.01 to about 25 weight percent, and the quantity of the water is in the range of about 35 to about 50 weight percent.

Preferably in an emulsion product, the lipophilic oleaginous material is selected from the group consisting of petrolatum, mineral oil, mineral jelly, lanolin, water-insoluble silicones, and mixtures thereof.

Preferably in an emulsion product, the emulsifier comprises on a 100 weight percent total emulsion basis:

(a) about 2 to about 20 weight percent of a lipophilic nonionic emulsifier, and (b) about 0.01 to about 10 weight percent of a hydrophilic emulsifier.

Preferably in such an emulsifier system, the lipophilic nonionic emulsifier is selected from the group consisting of fatty alcohols derived from fatty acids containing about 12 to about 24 carbon atoms and adducts of said fatty alcohols with alkylene oxides containing at least two and less than four carbon atoms per starting alkylene oxide molecule, and mixtures thereof.

Also, preferably in such an emulsifier system, the hydrophilic emulsifier is selected from the group consisting of amphoteric surfactants, zwitterionic surfactants, nonionic surfactants, anionic surfactants and mixtures thereof.

Optionally but preferably an emulsion product of this invention contains an effective hair conditioning amount of hair conditioner. Preferably such a hair conditioner can be selected from the group consisting of water-dispersible monomeric quaternary ammonium compounds containing a long chain aliphatic group having from about 20 to about 24 carbon atoms inclusive and salts thereof, quaternary nitrogen containing polymers and salts thereof, and mixtures thereof. Preferably also, such a hair conditioner is selected from the group consisting of behenyl trimethylammonium methosulfate, behenyl trimethylammonium chloride, and mixtures thereof.

Preferably, an emulsion product contains nitrogenous organic base that is formed in situ from guanidine carbonate in an amount of about 0.9 to about 2 weight percent based on total weight of the emulsion product through theoretical reaction with a stoichiometric amount of calcium hydroxide.

Typically, a hair straightening emulsion product of this invention is prepared from a preparation kit comprising an activator component and a cream emulsion component by admixing together these respective components. The weight ratio of the activator component to the cream emulsion component is sufficient to prepare the inventive emulsion product. Conveniently, in commerce, parts or all of the entire activator component are/is admixed with part or all of the entire cream emulsion component of a given kit by the user or preparer depending on the "strength" required for the user's hair type and amount of hair to be treated (for example, perhaps only on the new hair outgrowth or on entire hair). The exact weight ratio of activator component to cream emulsion component typically is thus usually pre-selected by the manufacturer and is unimportant to the user or preparer who simply follows the instructions of the manufacturer.

The activator component preferably comprises on a 100 weight percent total activator component basis about 10 to about 20 weight percent of the dissolved water-soluble salt of said nitrogenous organic base and about 80 to about 90 weight percent of water.

Preferably, the cream emulsion component used in the practice of this invention comprises on a 100 weight percent total cream emulsion component basis about 0.6 to about 1.6 weight percent of alkali metal hydroxide, about 2 to about 3.5 weight percent of alkaline earth metal hydroxide and about 35 to about 60 weight percent of water together with the lipophilic oleaginous material and the emulsifier.

Some of the emulsifier and some of the lipophilic oleaginous material can be present in the activator component if desired.

Thus, the arrangement is such that, when the activator component and the cream emulsion component are admixed together, the nitrogenous organic base and alkaline earth metal salt are conveniently formed in situ and an emulsion product of the invention is produced.

Preferably a hair straightening emulsion product of this invention has a shelf-life chemical stability of at least about one hour and a pH in the range of about 11.5 to about 14, and preferably of about 12 to about 13.

For convenience, the term "cream emulsion component" as used herein refers to highly alkaline oil-in-water emulsion containing an alkali metal hydroxide and an alkaline earth metal hydroxide. Preferably, a cream emulsion component contains about 3.5 weight percent calcium hydroxide or less in combination with no more than about 1.6 weight percent alkali metal hydroxide, preferably lithium hydroxide (anhydrous basis) and has a pH about 11.5. The term "cream" and "cream emulsion" are usable interchangeably in reference to a cream emulsion component for convenience. A cream emulsion component is preferably a viscous oil-in-water emulsion which is non-runny particularly when mixed with an activator solution. The term "precipitant" as used herein refers to an inorganic material such as an alkaline earth metal hydroxide the cation of which forms substantially water-insoluble stable salts, such as carbonates, sulfates, and the like. The term "hair straightening emulsion product" or "emulsion product" refers to the resulting admixture of the foregoing highly alkaline cream emulsion component and a liquid activator component.

For convenience, the term "activator component" as used herein preferably refers to an aqueous solution of a water-soluble salt of a relatively strong nitrogenous organic base with an anion capable of being precipitated by an alkaline earth metal ion as a substantially water-insoluble salt under highly alkaline conditions. Preferably, the activator component contains less than about 20% by weight guanidine carbonate.

A cream emulsion component is convertible to a hair straightening emulsion product when mixed with a liquid aqueous activator component.

Reference to weight percent throughout this specification is generally based on the dry solids weight percent of the individual ingredient present with reference to the total weight of the cream emulsion component composition, the activator component composition or the hair straightening emulsion product resulting from the admixture of the two, as the case may be.

As in commercial conventional no-lye type hair straightening products, the nitrogenous organic base is in the present invention released in sufficient hair straightening amount preferably just before use by the in situ reaction of guanidine carbonate with calcium hydroxide as the precipitant. For this purpose, calcium hydroxide is preferably emulsified in a cream emulsion form, and the guanidine carbonate is preferably present in the activator component as a separate aqueous activator liquid form. The activator component is combined with the cream emulsion component to form the hair straightening emulsion product just before application of the hair straightener to the hair.

Alternatively, the guanidine carbonate can be if desired, included in the cream emulsion component and the calcium hydroxide can be in an aqueous suspension added just before use, but this approach is less practical. The relatively high amount (>4%) of calcium hydroxide (based on total prior art cream emulsion weight) usually required for a precipitation reaction is difficult to suspend in concentrated substantially liquid form and could likely result after admixture in a non-uniform emulsion mixture which would not relax the hair properly. In commercial practice, therefore, guanidine carbonate preferably is present in the activator component of a two-component kit in substantially liquid form.

Until now, the cream emulsion component, prior to the addition of aqueous guanidine carbonate, generally contained an amount of calcium hydroxide generally between above about 4 and about 7 percent or more, and the activator component, prior to being added to the cream emulsion component, contained guanidine carbonate at generally between above about 20 and about 28 weight percent.

Other nitrogenous organic bases which may be used in place of free base guanidine and hydrated guanidine, (guanidine hydroxide, guanidinium hydroxide and the like), include N-methyl guanidine, dimethylaminoguanidine (sym. and asym.), acetamidine, dimethylaminoamidine, aminoamidine and acetamide. The nitrogenous organic base may be liberated from salts other than the carbonate salt, such as from a sulfate or sulfite, fluoride, oxalate, tartrate, laurate, stearate or alginate salt so long as the salt of the precipitant formed is substantially water-insoluble.

Other alkaline earth hydroxides, such as barium or strontium hydroxide may be used in place of calcium hydroxide to release free guanidine base and hydrated forms thereof from guanidine salt in water. Alkaline earth oxides may also be used, producing hydroxides when added to water.

It has now been surprisingly found that substantially complete permanent hair straightening can be achieved with the substantially decreased amounts of combined strong chemical bases that are here employed compared to prior art emulsions wherein these same bases are separately employed in operable amounts. The present emulsion products surprisingly employ respective amounts of strong chemical bases that are ineffective by themselves for hair straightening. For example, about one weight percent or less of alkali metal hydroxide, such as lithium hydroxide, sodium hydroxide and potassium hydroxide is employed. Lithium hydroxide is particularly preferred. For purposes of illustrating a conditioning hair straightening emulsion product, and not by way of limitation, remarks hereafter may refer to guanidine carbonate as the salt from which the nitrogenous organic base is formed in situ by reacting with calcium hydroxide and to lithium hydroxide as the alkali metal hydroxide since these are the presently preferred materials of most commercial interest.

Briefly described, the cream emulsion components of this invention prior to admixing with activator component comprise, on a 100 weight percent total cream emulsion weight basis, about 5% to about 65 weight percent of lipophilic oleaginous material; about 0.01 to about 25 weight percent of lipophilic emulsifier, hydrophilic emulsifier and mixtures thereof and the balance being water.

More particularly, a preferred cream emulsion component of this invention comprises, prior to admixing with activator, on a 100 weight percent total cream emulsion component weight basis:

(a) about 15 to about 40 weight percent of a lipophilic oleaginous material;

(b) about 3 to about 15 weight percent of a lipophilic nonionic emulsifier;

(c) about 0.01 to about 10 weight percent of a hydrophilic emulsifier;

(d) about 0.1 to about 10 weight percent of an aliphatic polyhydroxy compound which is liquid at room temperature;

(e) about 2 to about 3 weight percent of calcium hydroxide;

(f) about 0.5 to about 1 weight percent (anhydrous basis) of lithium hydroxide, the exact minimum amount used in this range being sufficient to produce a pH of at least about 11.5 in said emulsion; and (g) about 40 to about 45 weight percent water.

In one preferred conditioning hair straightening cream emulsion embodiment, the cream emulsion component additionally includes on a 100 weight percent basis of cream emulsion component about 0.01 to about 5 weight percent of at least one hair conditioning agent that is a water dispersible quaternary nitrogen containing polymer, a monomeric quaternary ammonium compound containing a long chain aliphatic group having from about 20 to about 24 carbon atoms inclusive and combinations thereof.

The term "highly alkaline," as indicated above, refers to a pH of from above about 11.5 to about 14, and preferably to a pH of above about 12.

The term "effective conditioning amount" means that a sufficient amount of hair conditioner is present in the emulsion product to effect discernible hair conditioning benefits during the chemical hair straightening step. The term "substantive conditioning" means that the hair conditioner is not removed by water rinsing so that a beneficial hair conditioned effect is discernible on the relaxed hair after the straightening process is completed and the emulsion product is rinsed from the hair with water. Preferably, substantive conditioning is discernible even after the straightened hair has been shampooed with a non-alkaline neutralizing shampoo and dried.

Hair conditioning effects are typically observed as a benefit during combing and detangling of wet hair during the hair straightening step of the process while the emulsion product is on the hair and while it is being rinsed from the hair with water. Substantive conditioning effects are typically a residual benefit also observable as improved stylability and manageability of the finished coiffure.

The term "hair conditioning agent" or "hair conditioner" as used herein refers to substantially water-soluble quaternary nitrogen containing compounds which under certain circumstances are substantive to hair. The term "conditioned effect" or "substantive conditioned effect" is used herein in its commonly understood meaning denoting desirable improvements in the characteristics of the hair over those same characteristics normally observed in the absence of the conditioning agent, such as easier combing of the wet or dry hair, increased luster, a silkier, smoother and softer tactile feel on the hair, more manageable setting and styling and the like.

The term "substantive conditioned effect" also encompasses one or more of the foregoing desirable characteristics which may be either apparent by a visual or tactile inspection of the straightened hair as well as characteristics which may only be measured objectively. For example, changes in the measured tensile strength of the straightened hair or microscopically visible changes in the hair's structure attributable to the presence of the cationic conditioning agent can show beneficial protective conditioning during the hair straightening process. Less hair damage, (i.e.) loss of hair from breakage, less splitting of the straightened fibers and like desirable characteristics are associated with protective conditioning of hair against the deleterious action of caustic materials.

The term "hair damage" as used herein means that hair fibers are either weakened and broken off or lost during or following the hair straightening treatment. Hair loss is determined by counting the number of fibers that collect in either the sink or on the comb. Some hair loss is normal and usually expected which is not attributed to the use of the straightener and a loss in the range of about 5 fibers or less is conventionally considered to be in the normal expected range. Hair loss in excess of that amount, therefore, tends to indicate that some undesirable weakening of the tensile fiber properties has occurred.

The term "hair condition" as used herein includes the subjective properties of hair such as luster, color, and desirable tactile properties as well as tensile fiber properties reflected as fiber breakage and a visibly straighter curl pattern. The term "tensile fiber properties" includes the physical and chemical characteristics of human hair associated with intact fiber integrity that, in turn, contribute to desirable mechanical properties of good hair condition, i.e., easy combability, manageability and "soft, smooth hand feel."

Thus, it is generally recognized that hair condition is a complex concept that depends on a variety of physical attributes that are subjectively evaluated by practitioners.

One important subjectively evaluated attribute is the natural color of the hair and the brightness of its tone. Discoloration or changes in hair color following an alkali-straightening procedure can be undesirable. For example, dark hair, especially dark brown and black hair, can become reddened, faded or dulled. Particularly troublesome is yellowing of natural white (gray) hair. Another important attribute that can be subjectively seen is an undesirable delustering of the natural sheen or luster associated with the previously described discoloration of the natural color of the hair.

One of the benefits of using the improved hair straightener emulsion of this invention is good hair condition and non-yellowing or substantial non-discoloration of treated hair. The mechanism of this invention is not fully understood. However, it is believed that the process protects and preserves those constituents in hair, other than cystine disulfide, that can be negatively affected or degraded as a function of time of exposure to alkali, and which contribute to color and sheen.

It is now recognized and is well appreciated by those skilled in the art that instrumental techniques can be employed to objectively measure the effect of permanent hair straightening on various tensile fiber properties of the hair, such as strength and breakage. Such techniques were used here as the examples below indicate.

One of the instrumental techniques employed measures the stress-strain modulus of hair in terms of fiber elongation and axial swelling while it is actually undergoing a chemical hair straightening procedure. This technique is the so-called Intermittent Modulus Technique (IMT). By the IMT, changes in the strength of the hair under an intermittently applied additional load are measured. A laboratory model of an intermittent modulus device for practicing the IMT was here constructed and employed.

The intermittent modulus device comprises a balance attached to a beam which controls illumination of a photocell and generates a current. Light control for the photocell is electronically regulated and current is measured on a strip chart recorder.

The instrument balance beam is attached to a test hair fiber. The hair fiber is anchored at each end by a vinyl tab and is laterally positioned. The lateral position of the fiber is controlled by a micrometer, and controls are provided on the instrument to assure exact fiber alignment. The length of the hair fiber for convenience is preferably of a gauge length of about 1.5 centimeters (about 0.6 inches) but is not so limited. A constant load is placed on the hair fiber and an additional load is applied at intermittent intervals. For example, a constant load of 0.5 grams can be applied, and additional loads of 0.5 grams can be applied at 30 second intervals.

Changes in length of the fiber cause proportional changes in the position of the recorder pen. Fiber axial swelling is influenced and controlled by applied chemical treatments thus making it possible to assess the treatment in terms of fiber axial swelling. Axial swelling changes are magnified 200 times on the recorder chart, so that a 30-millimeter (1.2 inch) pen excursion is equivalent to 1 percent change in fiber length for a fiber of about 1.5 centimeters gauge length.

Using this technique, therefore, fiber integrity was measured in terms of both fiber strength and fiber elongation. Fiber strength was determined by the height of the vertical pen excursion. For example, the greater the chemical attack, the weaker the fiber becomes and this is reflected by a greater vertical excursion by the pen. Fiber elongation is related to straightening and is reflected by changes in the vertical starting position of the pen on the recorder chart. Thus, shortening of the fiber as it weakens is readily observable. Restoration of fiber integrity is considered a reversal of weakened fiber strength and supercontraction.

The supercontraction time (SCT) of the hair can be readily determined by this technique as well as the total relaxation treatment (TRT) time (the point at which no further chemical hair straightening action occurs) from the graphic representation in fiber change. See for example, the discussion of the use of such a technique for measuring physicochemical changes in hair during hair waving by Garcia et al., "Letter to the Editor," *J. Soc. Cosm. Chem.*, 41, 149–154, (1990) the relevant components of which are incorporated herein by reference.

Hair fibers treated with hair straightening emulsion products of this invention demonstrated an SCT of less than about 15 minutes, preferably less than about 10 minutes and a TRT of less than about 25 minutes, preferably less than about 20 minutes. These SCT and TRT times were found to generally correlate with complete permanent hair straightening under practical actual use conditions. An SCT of longer than about 20 minutes or a TRT of longer than about 25 minutes generally was undesirable and typically found to correlate with loss of substantially complete permanent hair straightening resulting in either no hair straightening or at best some texturizing (partial permanent removal of the natural curl) of the hair.

It is recognized that, once the beneficial chemical straightening action which achieves substantially complete permanent hair straightening is achieved, any further unnecessary exposure of the hair to high alkalinity can be deleterious to the hair protein and hence its physical structure. Thus, based on data obtained employing the IMT, substantially complete permanent hair straightening was considered to be achieved by an emulsion product if it demonstrated an SCT of 15 minutes or less and a TRT of 25 minutes or less.

From our experience, calculated values of percent loss in tensile strength of hair that has been straightened with conventional highly alkaline "lye" type or conventional "no-lye" type hair straighteners obtained with the IMT data compare favorably with those obtained by commercially available tensile fiber testers, such as the Scott Tensile Tester, Model CRE-500 (GCA/Precision Scientific, Chicago, Ill.). Also in this regard, a description of the construction of a laboratory model of an analogous device used to study the performance of depilatories can be found in Elliot, "Use of a Laboratory Model to Evaluate the Factors Influencing the Performance of Depilatories," *J. Soc. Cosm. Chem.*, 25, 367–377, (1974).

The beneficial results as shown by the data obtained from the IMT have been further corroborated by improved tensile fiber properties determined with a Scott Tensile Tester and by subjective evaluations of hair condition as well as permanent hair straightening as described in the following examples.

Lithium hydroxide is commercially supplied as free-flowing crystals of lithium hydroxide monohydrate, assayed as about 57.2% lithium hydroxide. For convenience, references made herein to the term "lithium hydroxide" denote the monohydrate form as supplied and to the term "active lithium hydroxide" denote the anhydrous form. Likewise for convenience, references hereafter made to "weight percent" of lithium hydroxide, therefore, are expressed as lithium hydroxide monohydrate and references to "active" weight percent indicate the amount calculated as anhydrous lithium hydroxide.

For effective hair straightening with a hair straightening emulsion product of this invention, a cream emulsion component is employed that contains, prior to admixing with activator component, from about 2 to less than about 3 weight percent, preferably about 2.5 to about 2.75 weight percent calcium hydroxide, lithium hydroxide in an amount of from about 1 weight percent to less than about 2 weight percent, more preferably from about 1.25 weight percent to about 1.8 weight percent. These amounts of lithium hydroxide correspond, respectively, to an active weight percent of lithium hydroxide of from about 0.5 weight percent to about 1 weight percent, and more preferably from about 0.7 weight percent to less than about 1 weight percent in the cream emulsion component prior to admixing it with activator component. It is recognized that the exact minimum amount used should be at least sufficient to produce, in combination with the calcium hydroxide, a pH of at least about 11.5 in the cream emulsion component.

A preferred embodiment of an activator component comprises, prior to admixture with the cream emulsion component, about 10 to about 20 weight percent, more preferably about 11 to about 17 weight percent, guanidine carbonate. Preferably the activator component composition further includes water-soluble cosmetic adjuvants such as polyhydroxy compounds having from about 3 to about 6 carbon atoms and water-soluble derivatives thereof, thickening agents, metal-ion chelating agents and optionally hair conditioning agents, preservatives, perfume and product colorants. Aliphatic polyhydroxy compounds, such as propylene glycol, glycerine, sorbitol and water-soluble sorbitan derivatives are particularly preferred.

The pH of the activator component is preferably between about 11 to about 13, more preferably between about 11.5 to about 12. The viscosity of the activator component is preferably sufficiently liquid for relatively fast intimate mixing with a relatively stiff viscous highly alkaline cream emulsion component. However, the liquidity of the activator component should not thin the admixture to a runny state or conversely increase the viscosity of the admixture so that it becomes difficult to distribute through or remove from the hair.

The viscosity of the activator component is conveniently and preferably adjusted by including conventional thickening agents, such as xanthan gum and like natural gum thickeners, or by including conventional cationic polymers capable of thickening, such as POLYQUATERNIUM-4 and POLYQUATERNIUM-10.

It is recognized that a conditioning hair straightener system embodying the principles of this invention also can be practiced by incorporating a hair conditioner compound in the cream emulsion component, or alternatively by including a component of the total amount of hair conditioner agent desired in the activator component composition and the remaining amount in the cream emulsion component. It is also recognized that the hair conditioning agent can if desired be packaged as a liquid or in a powder form in a separate container and dissolved in either the liquid activator component just prior to mixing the activator component with cream emulsion component or in the emulsion product for use.

A particularly preferred activator component, which is intended to be mixed at a ratio of one part by weight activator to about 3.5 to about 6 parts by weight, preferably about 4 to about 5 parts by weight, cream emulsion component, comprises on a dry solid basis of the total weight of the activator component, prior to mixing, about 10 to about 17 weight percent guanidine carbonate, about 0.05 to about 0.5 weight percent sorbitol and sufficient thickening agent dissolved in water along with sufficient metal-ion chelating agent, if necessary. Optionally, the activator can contain sufficient colorant for tinting the appearance of the composition as well as preservative and fragrance.

Preferably a kit for a hair straightening product embodying the principles of this invention comprises at least two packages. For example, a first package can include an aqueous activator component as previously described. A second package can include an aqueous cream emulsion component containing the alkaline earth hydroxide and alkali metal hydroxide and having a pH of from at least about 11.5 to about 14. The contents of the first and second packages are admixed to provide a hair straightening emulsion product just before use.

In commercial practice, the hair straightening emulsion products of this invention are conveniently employed in three alkalinity levels, identified as "mild", "regular" and "super" in accord with normal commercial practice. The alkalinity strengths of the hair straightening emulsions of this invention can be adjusted, if desired, by controlling the amount of free organic base released upon the mixing of an activator component with a cream emulsion component. Thus, the cream emulsion component and the activator component each can be prepared commercially to contain calculated pre-selected amounts of co-reactants. Such components are then supplied to the user packaged in appropriate components that are ready to be mixed together before use, thereby to produce a desired alkaline strength in the emulsion product.

For example, in commerce, the no-lye type cream emulsion ingredients are typically supplied packaged in quantities of about 215 to about 225 grams. For use, the cream emulsion component is then mixed with about 40 to about 45 grams activator component to provide a mild strength emulsion product; with about 50 to about 55 grams of activator component to provide a regular strength emulsion product and with about 60 to about 65 grams of activator component to provide a super strength emulsion product. Mild strength emulsion product is generally employed if the hair is considered of fine texture or has been previously color treated; regular strength emulsion product is employed if the hair is considered to be of normal (medium) texture and super strength emulsion products is employed if the hair is considered to be of coarse to resistant texture which is generally resistant to chemical treatments. Hence, the hair type of the particular individual receiving a hair straightening treatment with an emulsion of this invention indicates the suitable amount of free organic base to be released in situ in the given emulsion product.

In the hair straightening emulsion products of this invention, the amounts of strong chemical base and other components can be expressed if desired on a molar basis. For example, the amount of free organic base calculated as free guanidine in the prepared emulsion product can be between about 0.08 to about 0.35 molar, and preferably between about 0.1 to between about 0.3 molar. In general, the amount of free organic base in an emulsion product is substantially lower by about half or less than the amount employed in a prior art emulsion that employs only free organic base as the sole strong organic base. The molar amount of free base guanidine preferred in present commercial practice is of about 0.5 to about 0.7 molar. Guanidine concentrations within the desired range are obtained in emulsion product of this invention from guanidine carbonate concentrations of between about 0.5 and 1.2 molar, preferably between about 0.6 to about 1 molar; calcium hydroxide concentrations of between about 0.25 to about 0.45 molar, preferably between about 0.3 to about 0.4 molar, and active lithium hydroxide (anhydrous basis) concentrations of between about 0.3 to about 0.45 molar, preferably between about 0.35 to about 0.4 molar.

In contrast, conventional commercial prior art lye-type hair straightening products contain mainly either sodium hydroxide or lithium hydroxide as the sole alkali metal hydroxide hair straightening agent. Such products require at least above about 0.5 molar concentration of alkali metal hydroxide for operability purposes.

Conventional commercial prior art non-lye type commercial hair straightening emulsion products containing greater than 1 weight percent active lithium hydroxide (anhydrous basis) are frequently augmented with calcium hydroxide as a pH buffer at a respective molar ratio in the range of about 2:1 to about 3:1. In contrast, the cream emulsion component of this invention, prior to admixing it with an activator component, contains a molar ratio of lithium hydroxide to calcium hydroxide of no more than about 1.2:1. When such a cream emulsion component is used with an activator component to prepare a hair straightening emulsion product, the concentration of active lithium hydroxide present in the emulsion product is less than about 1 weight percent. This low amount of lithium hydroxide is generally insufficient as the sole strong chemical base to effect substantially complete permanent hair straightening. Hence, by comparison, the level of hair straightening achieved with the emulsion products of this invention was judged surprising. Also surprising is the fact that, despite the presence of lithium hydroxide in combination with the strong nitrogenous organic base in a hair straightening emulsion product, skin irritation is not increased and hair condition is not adversely affected, as illustrated below.

Skin irritation is conveniently determined during the chemical hair straightening step of the process; i.e., while an emulsion product is being applied and is in contact with the hair. While care is taken to avoid contacting the scalp and facial skin areas of the hairline, some contact is unavoidable. Here, irritation of the scalp and skin was determined employing a "Skin Sensation Irritation" (SSI) rating scale during a salon application, based on the subjective volunteered verbal comments of the individual person receiving the hair straightener treatment reporting sensations of skin tingling, stinging, burning or some like discomfort or distress. The general SSI Rating scale employed is as follows:

| Rating | Skin Sensation Irritation |
| --- | --- |
| 1 | None; person does not complain either verbally or indicate by body language of any discomfort.. |
| 2 | Minor local tingling or at hairline, but person can withstand minor discomfort during total treatment time. |
| 3 | Sufficient discomfort to person to require that product be removed before hair is sufficiently straightened, but no scalp burns are present. |
| 4 | Person experiences severe sensation and/or scalp burns are present. |

An emulsion product giving an SSI Rating of 1–2 is judged commercially acceptable, whereas an SSI Rating of 3 is generally objectionable to undesirable and an SSI Rating of 4 is unacceptable.

It is recognized that the SSI Rating is also influenced by factors unrelated to the hair straightener composition itself. For example, if the user had previously abraded or scratched the scalp or skin during cleansing and grooming, the abraded or scratched area may be more predisposed to being irritated. Another factor, of course, is the person's health and their natural allergic predisposition to skin irritation by alkaline products and the person subjective opinion of discomfort.

Based on historical commercial experience with conventional no-lye type emulsions products SSI ratings of 1 are usually achieved for at least about 85% to about 90% of a given group receiving the treatment and such emulsion products are generally considered by the industry to be substantially non-irritating to skin.

As a threshold standard, therefore, emulsion products of this invention containing relatively low amounts of alkali metal hydroxide are judged commercially useful if SSI Ratings of 1 and 2 are shown for at least about 75% of a given group receiving the hair straightener treatment, preferably at least about 80% being given an SSI Rating of 1.

As discussed further below, it was found that, when a combination of long-chain ($C_{22}$) behenyltrimonium hair conditioning agent and POLYQUATERNIUM-6, a polyD-MDAAC polymer, was employed in the cream emulsion component, SSI Ratings of 1 were achieved on at least 85% of a given group. Also, substantive conditioning effects were achieved with the combination of conditioning agents which were more pronounced than those that were achieved when the POLYQUATERNIUM-6 was absent.

Surprisingly, when POLYQUATERNIUM-6 was used as the sole hair conditioning agent, the number of SSI Ratings of 1 were lower than when the combination of hair conditioners was employed. The reason for these results is not now fully understood and applicants do not wish to be bound by any one theory.

The choice of hair conditioning agent is believed to be limited only by its solubility and its ability to effect conditioning during the highly alkaline chemical relaxation step of the process or to produce a substantive conditioned effect on the relaxed hair, so long as it does not interfere with the action of the active hair relaxing agent.

A preferred water, soluble hair conditioning agent is a cationic quaternary ammonium compound which is substantive to the hair and retains a cationic positive charge at a pH above at least 12, more preferably at above about pH 13. Preferably, the hair conditioning agent is present in an emulsion product in an amount of about 0.01 to about 5 weight percent, more preferably about 0.05 to about 1.5 weight percent, and most preferably about 0.1 to about 1 weight percent, calculated on a dry solids basis of the total weight of the hair straightener composition.

Cationic conditioning compounds include any number of quaternary nitrogen containing polymeric and non-polymeric materials well known in the art. For example, cationic compounds include monomeric quaternary ammonium salts, quaternary nitrogen containing polymers and aminofunctional silicone polymers having a polar amine group which develops a net positive charge in an aqueous solution. Monomeric quaternary ammonium compounds containing an aliphatic group from about 20 to about 24 carbon atoms are preferred. Quaternary nitrogen containing polymers are preferred, and, in particular, those which can also modify viscosity as thickeners. The term "quaternary nitrogen containing polymer" as used herein denotes polymers having at least one available quaternary nitrogen atom per molecule.

A number of quaternary nitrogen-containing compounds, their manufacturers and general descriptions of their chemical characteristics can be found in the CTFA Dictionary and in the *International Cosmetic Ingredient Dictionary*, Vol. 1 and 2, 5th Ed., published by the Cosmetic Toiletry and Fragrance Association, Inc. (CTFA) (1993), the pertinent disclosures of which are incorporated herein by reference. The name assigned to the ingredients by the CTFA or by the manufacturer is used for convenience.

Particularly preferred are the non-polymeric long-chain length ($C_{22}$) quaternary ammonium compounds which are behenyltrimonium salts, such as behenyl trimethyl ammonium methosulfate (BTMS) identified by the CTFA name, BEHENTRIMONIUM METHOSULFATE and N,N,N-trimethyl-1-docosanaminium chloride (BTMC) identified by the CTFA name, BEHENTRIMONIUM CHLORIDE. These materials are sold commercially under the trademarks INCROQUAT BEHENYL® TMS and INCROQUAT® BEHENYL TMC by Croda Inc., New York, and VARISOFT by Witco Corp., New York.

BTMS and BTMC are commercially supplied as wax suspensions or solutions in cetearyl alcohol at an active quaternary concentration of about 24–26%. References to weight percent BTMS or to BTMC, therefore, refer to the material as supplied and reference to active weight percent refers to weight percent based on active quaternary concentration. An active quaternary weight percent concentration of about 0.5 to about 2 weight percent, preferably from about 0.75 to about 1.5 weight percent, and most preferably of about 1 to about 1.25 weight percent can be used for achieving conditioning benefits. The upper amount of behenyltrimonium compound generally is not limited other than by cost considerations.

Quaternized nitrogen-containing organic polymers which are particularly preferred for achieving substantive hair conditioning benefits are quaternary nitrogen-containing polymers prepared by the polymerization of a diallylamine, preferably dialkyldiallylammonium salt or copolymer thereof in which the alkyl group contains 1 to about 18 carbon atoms, and more preferably where the alkyl group is methyl or ethyl; copolymers containing a cationic component derived from the monomer of dialkyldiallylammonium salt and an anionic component derived from anionic monomers of acrylic acid and methacrylic acid, and polyampholyte terpolymers thereof having as the cationic component, a monomer which is a derivative of diallylamine, preferably a dimethyldiallylammonium salt, an anionic component derived from anionic monomers of acrylic acid or 2-acrylamido-2-methylpropane sulfonic acid and a nonionic component derived from nonionic monomers of acrylamide. Details concerning the preparation of such quaternary nitrogen containing polymers can be found, for example, in U.S. Pat. No. 3,288,770; No. 3,412,019; No. 4,772,462 and No. 5,275,809, the pertinent disclosures of which are incorporated herein by reference.

Particularly preferred are the chloride salts of the foregoing quaternized homopolymers and copolymers in which the alkyl group is methyl or ethyl, which are available in a range of weight average molecular weights as aqueous compositions containing about 40 percent polymer solids sold under the trademark MERQUAT® by The Calgon Corporation, subsidiary of Merck & Co., Pittsburgh, Pa.

For example, the homopolymer, dimethyldiallyl ammonium chloride (polyDMDAAC) has the CTFA name, POLYQUATERNIUM-6, is described as having a weight average molecular weight of approximately 100,000 and is sold under the trademarks MERQUAT®-100 by The Calgon Corporation and ALCOFIX® 131 by Allied Colloids Inc., Suffolk, Va. It is well known that substantive conditioning effects can be produced when POLYQUATERNIUM-6, is present as an ingredient in a no-base, alkali hair straightener. Such products have been patented and commercialized by the assignee of this invention. However, it has now surprisingly been found that about half of the amount of POLYQUATERNIUM-6 normally used in a no-lye hair straightener can produce substantially equivalent substantive conditioning effects when it is used in combination with the non-polymeric conditioner, BTMS, in the no-lye straightener products of this invention.

Other useful copolymers include a copolymer reaction product of DMDAAC with acrylamide monomers having the CTFA name, POLYQUATERNIUM-7, which is described has having a weight average molecular weight of approximately 500,000 and is sold under the trademark MERQUAT®-550. Another copolymer is the reaction product comprised of 80 percent by weight DMDAAC and 20 percent by weight of an anionic monomer of acrylic acid, has the CTFA name, POLYQUATERNIUM-22, is described as having a weight average molecular weight of about 1,300,000 and is sold under the trademark MERQUAT®-280. Details for the preparation of POLYQUATERNIUM-22 and its related polymers is described in U.S. Pat. No. 4,772,462 issued to Boothe et al., the pertinent disclosures of which are incorporated herein by reference.

Also useful is an ampholyte terpolymer comprised of a nonionic component derived from the monomer acrylamide (AM), a cationic component derived from the cationic monomer dimethyldiallylammonium chloride (DMDAAC), and an anionic component derived from the anionic monomer of acrylic acid (AA) or 2-acrylamido-2-methylpropane sulfonic acid (AMPSA) or combinations of AA and AMPSA, described as having a weight average molecular weight of from about 10,000 to about 10 million. An exemplary terpolymer is sold under the trademark MERQUAT® PLUS in varying viscosity grades, identified by the CTFA name POLYQUATERNIUM-39. Details for the preparation of such terpolymers is described in U.S. Pat. No. 5,275,809 issued to Chen et al., the pertinent disclosures of which are incorporated herein by reference. POLYQUATERNIUM-6 is particularly preferred.

Other useful polymeric quaternary ammonium salts are the homopolymer and the 2-propenamide polymer of ethanaminium, which is structurally identified as N,N,N-trimethyl-2-[(2-methyl-1-oxo-2-propenyl)Oxy]chloride and which are respectively identified by the CTFA names, POLYQUATERNIUM-37 and POLYQUATERNIUM-32, are sold under the trademarks SALCARE® SC95 and SALCARE® SC92 by Allied Colloids, Suffolk, Va. POLYQUATERNIUM-32 is particularly preferred.

Still other useful copolymers having a cationic ionic charge are sold under the trademark PERCOL® by Allied Colloids, Suffolk, Va. in approximate monomer ratios of about 60/40 to about 40/60 of dimethylaminoethyl acrylate/acrylamide polymer.

Other useful polymeric conditioners include cationic copolymers of methylvinylimadazolium chloride and vinyl pyrrolidone, sold commercially by BASF Aktiengesellschaft, West Germany under the trademark LUVIQUAT® at three comonomer ratios, namely at ratios of 95/5, 50/50 and 30/70 methylvinylimidazolium chloride to polyvinylpyrrolidone. These copolymers at all three comonomer ratios have the CTFA name POLYQUATERNIUM-16.

Other useful polymeric conditioning agents also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named POLYQUATERNIUM-10 in the CTFA Dictionary. Also useful are quaternized copolymers of hydroxyethylcellulose and dimethyldiallylammonium chloride, having the CTFA name POLYQUATERNIUM-4, sold in varying molecular weights under the trademark CELQUAT® by National Starch and Chemical Corporation, Bridgewater, N.J.

It is understood that a number of other polymeric conditioning agents which are commercially available can also be used. The present disclosure of the preferred polymeric conditioning agents is not intended to limit the scope of this invention.

The polymeric quaternary nitrogen-containing conditioning agent can be present at about 0.05 to about 5 weight percent, more preferably at about 0.1 to about 1.5 weight percent, most preferably at about 0.5 to about 0.75.

A highly alkaline conditioning cream emulsion component of a two-component hair straightening system is preferably prepared as an oil-in-water emulsion which is phase-stable on aging for a commercially useful lifetime. The term "phase-stable", as used herein, means that the cream emulsion component does not visibly de-emulsify or separate into distinct phases on storage aging at ambient temperature for at least about four weeks or on accelerated storage aging at about 45° C. for at least about 1 week, and preferably at least about 3 months. For purposes of illustrating this invention, the foregoing time period is considered indicative of a commercially useful lifetime in the field.

In actual practice, however, cream emulsion components prepared according to this invention preferably employ relatively low amounts of non-water ingredients and are relatively viscous creams which remain phase-stable and viscous on storage aging as described above. These compositions thereby provide cream emulsion components having concentrations of active ingredients that remain substantially constant throughout their useful lifetimes.

The term "non-water ingredients" as used herein refers to all co-emulsified ingredients, other than water. A "relatively low amount" means that the emulsion-forming ingredients and the alkaline material together preferably make up not more than about 65 weight percent on a dry solids basis of the total weight of the cream emulsion component. The term "relatively viscous cream" as used herein defines a cream emulsion component having a Brookfield viscosity of about 100,000 to greater than about 900,000 centipoises (cps), as measured with a model RVT Helipath spindle No. TE rotating at 5 revolutions per minute (rpm) for one minute at about 25° C.

Useful oleaginous material predominantly include petrolatum, mineral oils and mineral jellies, but can also include lanolin, water-insoluble silicones and like unctuous emulsifiable materials.

Useful petrolatum is available in several grades based upon both viscosity, melting point and color. The Saybolt seconds universal viscosities (S.S.U) of these products range from between about 50 and about 90 (50/90) S.S.U. at 210° F. (98.9° C.). Preferably, a colorless or "white" product having a Saybolt viscosity of about 55/75 S.S.U. at 210° F. (98.9°) and melting points in the degree range of 135°/140° F. (59.2°/60° C.) and 127°/137° F. (52.2°/57.8° C.) are used. Preferably, a grade that meets the standards of the United States Pharmacopeia (U.S.P.) is used.

Mineral oils useful herein are preferably U.S.P. grade white oils. Preferably, a colorless or "white" oil is used having reported typical Saybolt viscosities at 100° F. (37.8° C.) of about 50/350 S.S.U. and specific gravities at 77° F. (24.8° C.) of about 0.822 to about 0.895 (0.822/0.895). The materials having Saybolt viscosities of about 50/60 S.S.U. at 100° F. (37.8° C.) and specific gravities in the ranges 0.822/0.833 at 77° F. (24.8° C.) are preferred. In addition, a mineral jelly compounded of white petrolatum, white mineral oil and wax may also be used as an oleaginous material in the compositions of this invention.

The oleaginous materials may be present in a product emulsion (100 weight percent basis) at about 5 to about 40 weight percent. However, the percentage actually used in a product depends upon the desired product consistency.

For achieving or maintaining phase stability, a lipophilic modified hectorite clay gellant of the type disclosed, for example, in U.S. Pat. Nos. 4,390,033; 4,237,910; 4,524,787; 4,950,485; 5,068,101; 5,171,565 and 5,376,364 optionally can be employed. Phase-stable, relatively viscous creams can be prepared with amounts of up to about 3 weight percent, preferably of up to about 2 weight percent, of these clay gellants based on total weight of cream emulsion component.

Where present, lipophilic hectorite clay gellants are preferably incorporated in pre-gelled form for convenience, as they are known in the art to be difficult to prepare. Pre-gelled oleaginous products containing the above clay gellants are commercially designated by their manufacturer as mastergels.

The mastergels are preferably comprised of hectorite clays modified with (1) a quaternary nitrogen-containing compound such as Stearalkonium chloride or Quaternium-18 which contains at least one $C_8$–$C_{20}$ chain substituent having about 8 to about 20 carbon atoms on the quaternary nitrogen atom, (2) propylene carbonate, and (3) a non-polar organic liquid. Examples of such non-polar organic liquids include but are not limited to mineral spirits, mineral oil, glycerides, such as castor oil, a mixture of lanolin oil and isopropyl palmitate, and the like. Stearalkonium chloride and Quaternium-18 are defined in the CTFA Dictionary at pages 704 and 631–632 respectively.

Specific, useful lipophilic hectorite clay gellants which are commercially available as mastergels include: Bentone Gel MIO, comprised of mineral oil, propylene carbonate and QUATERNIUM-18 hectorite; Bentone Gel CAO, comprised of propylene carbonate, castor oil and Stearalkonium hectorite; Bentone Gels SS71 and S130, comprised of mineral spirits (ligroin or petroleum spirits having a boiling range of about 318°–400° F.), propylene carbonate and QUATERNIUM-18 hectorite; and Bentone Gel Lantrol, comprised of propylene carbonate, a mixture of lanolin oil (dewaxed lanolin) and isopropyl palmitate, and Stearalkonium hectorite. The above hectorite clay gellants may be individually used, may be interchanged, one for the other in a given composition, or may be mixed together in a composition.

The foregoing mastergels are commercially available from NL Chemical/NL Industries, Inc., Hightstown, N.J. According to that supplier's product brochures, these mastergels contain about 10 percent modified clay gellant, about 86.7 percent non-polar organic liquid and about 3.3 percent propylene carbonate based on total weight of mastergel as supplied.

Thus, the lipophilic-modified hectorite clay gellant may be present in the cream emulsion component of this invention in amount ranges from zero to up to about 3 weight percent, preferably up to about 2 weight percent, based on total cream emulsion weight.

Useful lipophilic emulsifiers preferably are nonionic emulsifiers which are commercially sold as balanced blends comprising lipophilic fatty alcohols (some distilled or double distilled) derived aliphates from fatty acids containing about 12 to about 24 carbon atoms and adducts thereof with alkylene oxides containing at least two and less than four carbon atoms per starting alkylene oxide. Ethylene oxide adducts are preferred. Particularly preferred are emulsifying waxes containing about 14 to about 20 carbon atoms, more preferably about 16 to about 18 carbon atoms. The term "emulsifying wax" denotes solid nonionic emulsifiers known in the art that are prepared as a mixture of fatty alcohols having from about 12 to about 24 carbon atoms, preferably predominantly lipophilic fatty alcohols having from about 14 to about 20 carbon atoms. Alternatively, the lilophilic nonionic emulsifier can be a balanced blend of the individual lipophilic fatty alcohols, each having about 14 to about 20 carbon atoms, more preferably about 16 to about 18 carbon atoms. Particularly useful fatty alcohols include cetyl alcohol, stearyl alcohol, tallow fatty alcohols and like saturated monovalent linear alcohols obtained from vegetable sources, animal oils and fats and blends thereof.

Preferably, emulsifying waxes meet the standards of the National Formulary (N.F.) or British Pharmacopeia (B.P.) and can be either the non-self-emulsifying or the self-emulsifying type. Self-emulsifying waxes are typically prepared with an auxiliary hydrophilic nonionic emulsifier present. The hydrophilic nonionic emulsifiers present are usually polyoxyethylene derivatives of fatty acid esters of sorbitol and sorbitol anhydride. Preferred are polysorbates which generally comprise mixtures of oleate or stearate esters condensed with ethylene oxide.

A preferred N.F. grade emulsifying wax is prepared from cetostearyl alcohol containing a polyoxyethylene derivative of a fatty acid ester of sorbitan. This material is known as Emulsifying Wax N.F. and is a creamy white, wax-like solid which is freely soluble in ether, chloroform, alcohol and most hydrocarbon solvents, but is insoluble in water. It melts at a temperature between 48° C. and 52° C., has a hydroxyl value between 178 and 192, an iodine value not more than 3.5, a saponification value not more than 14, and a pH (in a dispersion of 3 parts in 100 parts of water) between 5.5 and 7.0. Emulsifying Wax N.F. is commercially available from a number of suppliers. Exemplary and preferred materials are sold under the name POLAWAX by Croda, Inc., New York, N.Y.; and LIPOWAX P by Lipo Chemicals, Inc., Paterson, N.J.

Particularly preferred are tallow fatty alcohols manufactured and sold under the trademark HYDRENOL D or DD by Henkel KGaA, West Germany. According to the manufacturer, these materials comprise zero–2 percent $C_{12}$; 3–7 percent $C_{14}$; 25–35 $C_{16}$; 60–70 percent $C_{18}$; and zero to 2 percent $C_{20}$ moieties; less than 1.2 percent hydrocarbons, less than 0.3 percent water; and has an acid value of less than 0.1; a saponification value of less than 1.2; an iodine value of less than 1; a hydroxyl value of 210–220; and solidifies in the range of 48°–52° C. Another preferred nonionic emulsifier is a fatty alcohol mixture containing cetyl and stearyl alcohols sold under the trademark TA1618F by The Proctor & Gamble Company Industrial Chemicals Divisions, Cincinnati, Ohio.

In the practice of this invention, useful lipophilic nonionic emulsifiers are generally present at about 3 to about 15 weight percent, preferably at about 5 to about 12, more preferably at about 6 to about 10, based on total cream emulsion weight.

Useful hydrophilic emulsifiers are water-dispersible and water-soluble amphoteric surfactants, zwitterionic surfactants and nonionic surfactants. Anionic surfactants are also useful providing they do not negate the positive charge (cationic properties) of quaternary-nitrogen containing conditioning agents (if present).

A zwitterionic surfactant contains both cationic and anionic moieties in the same molecule, which form inner salts. Amphoteric surfactants that become anionic at alkaline pH and zwitterionic surfactants are preferred.

Useful zwitterionic surfactants include betaines and the related amphoteric sultaines derived from amino propane sulfonic acids. Examples of commercially available betaines include but are not limited to cocamidopropyl betaine, lauramidopropyl betaine, oleamidopropyl betaine, isostearamidopropyl betaine, coco betaine, cetyl betaine, oleyl betaine, coco/oleamidopropyl betaine, tallow dihydroxyethyl betaine, wheat germamidopropyl betaine and the like. Particularly preferred is cocamidopropylbetaine. Examples of commercially available sultaines include but are not limited to cocamidopropyl hydroxysultaine, lauryl hydroxysultaine and the like.

Suitable amphoteric surfactants include alkylamphocarboxypropionates, and alkylamphoglycinates having mono- or di-carboxyl groups derived from fatty acids having about 10 to about 22 carbon atoms in the fatty alkyl chain. Particularly preferred is stearoamphoglycinate, the CTFA name for 2-heptadecyl-1-carboxymethyl-1-(2-hydroxyethyl)-2-imidazolinium chloride, sold under the trademark Miranol® DM by the Miranol Chemical Company, Inc., South Brunswick (Dayton), N.J. Additional amphoteric surfactants include the class having an aminopropionate structure, such as N-fatty alkyl beta propionic acid and alkali metal salts thereof. Commercial materials having lauryl, myristyl, coco and tallow fatty alkyl groups are sold commercially under the tradename DERIPHAT® by General Mills Chemicals, Inc., Cosmedia Group, Minneapolis, Minn.

Nonionic surfactants include polyoxyethylene derivatives of fatty acid esters of sorbitol and sorbitol anhydride; polyethylene glycol esters of fatty acids, polyoxyethylene ethers of fatty alcohols, polyethylene oxide-polypropylene oxide condensates and polyoxyethylene lanolin ethers, and the like. Particularly preferred is the polyethylene glycol derivative of lanolin with an average of 75 moles of ethylene oxide identified by the CTFA name, PEG-75 LANOLIN.

Useful anionic emulsifiers may be illustrated by polyoxyethylene oleyl ether phosphates having about 3 to about 20 oxyethylene groups, sodium lauryl sulfate, and the stearic acid anion and the like. Polyoxyethylene (3) oleyl ether phosphate is particularly preferred.

Hydrophilic emulsifiers can be present at about 0.01 to about 10 weight percent, preferably at about 0.5 to about 5 weight percent, more preferably at about 1 to about 3 weight percent, based on total cream emulsion weight.

Useful aliphatic polyhydroxy compounds are water dispersible and contain about 3 to about 6 carbon atoms and are normally liquid at ambient room conditions, such as propylene glycol, glycerin, butylene glycol, hexylene glycol, sorbitol and the like. Particularly preferred is propylene glycol. The aliphatic polyhydroxy compounds can be present at about 0.1 to about 10 weight percent, preferably at about 1 to about 8 weight percent based on cream emulsion weight.

A conditioning hair straightener cream emulsion component can also include known cosmetic adjuvants, such as auxiliary emollients, viscosity modifying thickening agents, perfumes, preservatives, and product colorants.

Good conditioning was achieved with the conditioning hair straighteners of this invention when BTMS or BTMC were employed and conditioning was augmented by the inclusion of POLYQUATERNIUM-6 without loss of improved skin tolerance benefits. Additionally, no yellowing of natural white "gray" hair was noted.

The cream emulsion components may be prepared by any emulsion forming technique, such as by inversion or non-inversion methods.

For example, inversion emulsification is achieved by separately preparing an oil phase containing the substantially anhydrous lipophilic materials and clay gellant, where present, heating and mixing the foregoing materials at a temperature of about 80° C. and about 85° C. until a substantially homogeneous uniform oil phase results; separately preparing an aqueous (water) phase containing the substantially water-soluble components, except for the alkali metal hydroxide and perfume, where present, similarly heating and mixing the foregoing materials until a substantially homogeneous uniform water phase results.

Subsequently, the oil phase and the water phase are combined while maintaining the foregoing said temperature and mixing until a uniform main emulsion batch is obtained.

The main emulsion batch is then cooled to a temperature of about 55° C. to about 65° C. and the alkali metal hydroxide and hair conditioner, where present is added, mixing and maintaining the foregoing temperature until a homogeneous highly alkaline cream emulsion is obtained. The highly alkaline cream emulsion is preferably dearated and then cooled to about ambient room temperature of about 25° C. and any remaining optional ingredients, such as perfume are added and mixed into the highly alkaline cream emulsion. On reaching ambient temperature, the resulting viscous cream emulsion can be homogenized by conventional techniques, such as by versation under vacuum or ultrasonic mixing.

For use in a hair straightening procedure, a cream emulsion component is mixed with an activator component in proportions that produce free organic base and the other strong chemical bases in an emulsion product so that such product substantially completely permanently straightens hair within the limits disclosed herein.

It has been surprisingly found that an admixture comprised of about 3.5 to about 6 parts by weight of a cream emulsion component of this invention with one part by weight of an activator component comprising guanidine carbonate at about 10 to about 20 weight percent, preferably about 11 to about 17 weight percent, prior to admixture, provides substantially complete permanent hair straightening. The cream emulsion component, prior to mixing, comprises no more than about 1 active weight percent lithium hydroxide (anhydrous) and no more than about 3 weight percent calcium hydroxide. The reason for the improved hair straightening effect is not fully understood.

When employing the permanent hair straightening emulsion products of this invention in a hair straightening procedure, it is preferable that the person (such as a model) on whose head the compositions are used (the model) not wash her (or his) hair for at least 24 hours prior to the straightener treatment. This preference stems from the scalp protecting effect produced by the model's own sebum secretions. In addition, while washing the hair, slight physical damage can occur to the scalp which can become aggravated by the alkalinity of the hair straightener.

The model's hair is divided into four sections as delineated by the areas separated when hypothetical lines are drawn from ear-to-ear and from nose-to-backbone. Starting with the rear section, the straightener cream is applied to the hair with the back or smooth side of a comb (opposite from the teeth). Care is taken to avoid putting the composition on the scalp and about ⅛–¼ inch of the root end (lower component) of the hair shaft. This process takes about 8 to about 9 minutes for treatment of all the model's hair.

Each section of the hair is then physically smoothed with the comb back. At this time in the treatment, the scalp and lower sections of the hair shafts are contacted with the hair straightening emulsion product. The smoothing step helps to ensure adequate hair shaft penetration and softening by the emulsion product and also puts tension on the hair to help in straightening the hair. The smoothing step is then repeated to facilitate straightening. The total time for smoothing (both the initial and the repeat steps) normally takes from about 5 to about 10 minutes, depending upon the hair length and thickness. Thus, at the time of the repeat smoothing step, the emulsion product is on the head for about 13 to about 18 or even about 20 minutes.

The emulsion product is then thoroughly and rapidly removed from the hair by rinsing with water having a temperature of about 37° C. The rinsing step is followed by a shampooing with a non-alkaline shampoo. The shampoo is preferably buffered on the acid side of neutral at about pH 4 to about 6 so that residual alkali left in the hair or on the scalp is neutralized. This shampooing step is usually repeated two to three times.

After shampooing, the hair may be further treated with a conditioner to improve wet combing and hair feel. When the conditioning hair straightening emulsion products of this invention are used, no extra conditioning step is needed. The hair may then be set, styled and dried in a desired coiffure as is known in the art.

The following Examples illustrate cream emulsion components and hair straightening emulsion products of this invention with generally preferred ingredients but the Examples are not intended to be limited thereby. In all of the following Examples, where an emulsion product of this invention is prepared for use, liquid aqueous activator components are employed which contain about 0.1 to about 0.2 weight percent xanthan gum thickener, about 0.1 to about 0.2 weight percent sorbitol, (based on total activator component weight) optionally are tinted and are compositionally substantially the same, except for the amount (quantity) of guanidine carbonate salt present, as indicated. The proportion of activator component admixed with cream emulsion component is determined by the desired amount of available free nitrogenous organic base, the desired amount of alkaline earth metal hydroxide and the desired amount of available alkali metal hydroxide all to be present in the resulting emulsion product. The desired amount of alkaline earth metal hydroxide that is initially available for reaction with the guanidine carbonate is also considered.

EXAMPLES 1–9

Example Nos. 1–9 as shown in Table I illustrate the composition of conditioning cream emulsion components, each employing the hair conditioning agent, POLYQUATERNIUM-6.

Each of the cream emulsion components is convertible to a hair straightening emulsion product by mixing with liquid activator component containing guanidine carbonate in an amount, prior to mixing, of between about 10 to about 20 weight percent. Preferably, the activator component contains between about 11 to about 17 weight percent guanidine carbonate, based on total weight of activator component.

For example, a hair straightening emulsion product can be formed by mixing 1 part by weight activator component with: (a) about 5 parts by weight cream emulsion component to form a "Mild" strength emulsion product; (b) about 4 to about 4.5 parts by weight of cream emulsion component to form a "Regular" strength emulsion product and (c) about 3.5 parts by weight cream emulsion component to form a "Super" strength emulsion product.

TABLE I

| Ingredients | Weight Percent, Dry Solid Basis | | | | | | | | |
|---|---|---|---|---|---|---|---|---|---|
| | Ex 1 | Ex 2 | Ex 3 | Ex 4 | Ex 5 | Ex 6 | Ex 7 | Ex 8 | Ex 9 |
| 1. Petrolatum | 15 | 15 | 15 | 16.25 | 16.25 | 16.25 | 16.25 | 17 | 17 |
| 2. Mineral Oil | 10 | 10 | 10 | 11.25 | 11.25 | 11.25 | 11.25 | 12 | 12 |
| 3. Cetearyl alcohol (Note 1) | 11 | 11 | 11 | 11 | 11 | 11 | 11 | 11 | 11 |
| 4. Modified Hectorite Clay Gellant (Note 2) | 2 | 2 | 2 | 2 | 2 | 2 | 2 | 2 | 2 |
| 5. Amphoteric emulsifier (Note 3) | 0.5 | 0.5 | 0.5 | 0.5 | 0.5 | 0.5 | 0.5 | 0.5 | 0.5 |
| 6. PEG-75 Lanolin (Note 4) | 1.5 | 1.5 | 1.5 | 1.5 | 1.5 | 1.5 | 1.5 | 1.5 | 1.5 |
| 7. Propylene glycol | 5 | 5 | 5 | — | — | — | — | — | — |
| 8. POLYQUATERNIUM-6 (Note 5) | 1.26 | 1.26 | 1.26 | 1.6 | 1.6 | 1.6 | 1.6 | 1.26 | 1.26 |
| 9. Calcium hydroxide | 2.5 | 2.5 | 2.5 | 2.5 | 2.5 | 2.48 | 2.5 | 2.58 | 2.64 |
| 10. Lithium hydroxide monohydrate (Note 6) | 1.25 | 1.5 | 1.75 | 1.75 | 1.75 | 1.7 | 1.75 | 1.5 | 1.5 |
| 11. Perfume | Q.S. | Q.S. | Q.S. | Q.S. | — | Q.S. | Q.S. | — | — |
| 12. Water, deionized to 100 percent | Q.S. | Q.S. | Q.S. | Q.S. | Q.S. | Q.S. | Q.S. | Q.S. | Q.S |

Notes to Table I
Note 1. CTFA name for a fatty alcohol mixture containing cetyl alcohol and stearyl alcohol sold under the trademark TA 1618F by the Procter & Gamble or a tallow fatty alcohol sold under the trademark HYDRENOL D by Henkel GKaA, Germany which may be used.
Note 2. A modified hectorite clay gellant sold by N.L. Industries, Inc. under the trademark Bentone Gel MIO, Benton Gel CAO, Bentone Gel SS71, Bentone Gel S130 and Bentone Gel Lantrol may be used.
Note 3. Preferably stearamphoglycinate available from the Miranol Chemical Company, Inc., South Brunswick, NJ, under the trademark Miranol DM as a 20–27 percent active aqueous paste.
Note 4. CTFA name for Polyoxyethylene (75) lanolin, available as a 50 percent active water solution under the trademark LANETO 50 from the R.I.T.A. Corporation or SOLAN JP from Croda, Inc., or as a flake solid under the trademark LANETO 100 from R.I.T.A. Corporation.
Note 5. CTFA name for poly(DMDAAC) available under the trademarks Merquat-100 as a 40 percent active aqueous solution from Merck & Co., Inc. and ALCOFIX ® 131 as a free flowing bead powder from Allied Colloids, Inc.
Note 6. Typical reported chemical analysis is 57.2% as LiOH. May be added in dry form or as a concentrated aqueous solution.

The cream emulsion components are preparable by inversion and non-inversion emulsion techniques. For example, the oil phase and aqueous phase (water phase) were each separately prepared. The oil phase contained ingredients nos. 1–4 and the water phase contained ingredients nos. 5–9 and 12. Each phase was prepared in a heatable container equipped with appropriate propeller-type and paddle scraper mixers, heating each phase to preferably between about 70° C. and about 80° C., and subsequently combining the oil and water phase together.

The temperature of the combined phases was then maintained at about 70° C. to about 80° C. under continued relatively rapid agitation until a homogeneous emulsion formed. The resulting emulsion was allowed to deaerate, if necessary, and then was preferably cooled to between about 60° C. and about 55° C. while maintaining moderate agitation. Ingredient no. 10 was then added slowly with mixing agitation until a homogeneous cream emulsion component formed. For convenience, ingredient no. 10 may be predissolved in water and added as a concentrated solution of about 35 to about 55 weight percent. The cream emulsion component was then cooled to between about 40° C. and about 48° C., sampled for lithium hydroxide analysis and adjusted as needed. A perfume ingredient, if present, was then added with mixing agitation and the completed cream emulsion component was then force cooled to about ambient room temperature of about 25° C., subsequently optionally homogenized and packaged.

Viscous, phase stable cream emulsion components were obtained having a pH of about 11.5 to about 12.5.

EXAMPLES 10–15

The following Table II illustrates in Examples 10–12 cream emulsion components containing, as hair conditioners, a long chain ($C_{22}$) behenyl trimonium compound in combination with POLYQUATERNIUM-6. Example 13 is a cream emulsion component containing no hair conditioning agent and Examples 14 and 15 are cream emulsion controls containing no calcium hydroxide.

The cream emulsion components are preparable in the same manner as described in Examples 1–9.

TABLE II

| Ingredients | Weight Percent, Dry Solid Basis | | | | | |
|---|---|---|---|---|---|---|
| | Ex 10 | Ex 11 | Ex 12 | Ex 13 | Ex 14 | Ex 15 |
| 1. Petrolatum | 19 | 19 | 19 | 19 | 20 | 20 |
| 2. Mineral Oil | 16 | 16 | 16 | 16 | 16 | 16 |
| 3. Cetearyl alcohol (Note 1 - Table I) | 6 | 6 | 6 | 11 | 6 | 6 |
| 4. Modified Hectorite Clay Gellant (Note 2 - Table I) | 2 | 2 | 2 | 2 | 2 | 2 |
| 5. Cocamido propylbetaine (Note 7) | 0.55 | 0.55 | 0.55 | 0.55 | 0.55 | 0.55 |
| 6. PEG-75 Lanolin, (Note 4 - Table I) | 1.5 | 1.5 | 1.5 | 1.5 | 1.5 | 1.5 |
| 7. Propylene glycol | 1 | 1 | 1 | 1 | 1 | 1 |
| 8. Behentrimonium methosulfate in cetearyl alcohol (Note 8) | 5 | 5 | 5 | — | 5 | 5 |
| 9. POLYQUATERNIUM-6 (Note 5 - Table I) | 0.65 | 0.65 | 0.65 | — | 0.65 | 0.65 |
| 10. Calcium hydroxide | 2.7 | 2.7 | 2.7 | 2.7 | — | — |
| 11. Lithium hydroxide monohydrate (Note 6 - Table I) | 1.8 | 1.7 | — | 1.7 | 1.7 | — |
| 12. Sodium hydroxide | — | — | 1 | — | — | 1 |

TABLE II-continued

| | Weight Percent, Dry Solid Basis | | | | | |
|---|---|---|---|---|---|---|
| Ingredients | Ex 10 | Ex 11 | Ex 12 | Ex 13 | Ex 14 | Ex 15 |
| (Note 9) | | | | | | |
| 13. Perfume | Q.S. | Q.S. | Q.S. | Q.S. | Q.S. | Q.S. |
| 14. Water, deionized to 100% | Q.S. | Q.S. | Q.S. | Q.S. | Q.S. | Q.S. |

Notes to Table II
Note 7. CTFA name for cocamido propyldimethyl glycine available as a 30–35% active aqueous solution from Rhone-Poulenc under the trademark MIRATAINE ®.
Note 8. CTFA name for behenyltrimethyl ammonium methosulfate added as supplied as a wax suspension or solution of about 24–26% active quaternary in cetearyl alcohol under the trademarks INCROQUAT BEHENYL TMS from Croda Inc. and VARISOFT BTMS from Witco Corporation.
Note 9. Added as a 50% active aqueous solution.

EXAMPLE 16

This example compares the substantially complete permanent hair straightening efficacy of conditioning hair straightening emulsion products of this invention, the beneficial affects on the tensile strength characteristics and the conditioning of the straightened hair compared to a commercial two-component, no-lye type conditioning hair straightening emulsion product (this product being prepared by admixing together the two components). The two components of the commercial hair straightening kit consisted of a highly alkaline cream emulsion component containing about 5.1 weight percent calcium hydroxide and, as a hair conditioner, POLYQUATERNIUM-6 and a separate liquid activator component containing about 28% guanidine carbonate.

Preparation of Emulsion Product of This Invention

Each of the emulsion products was prepared for evaluation by mixing the cream emulsion component of either Example 11 or Example 10 with a liquid activator component, the latter respectively comprising, prior to mixing, either 11 weight percent or 13 weight percent guanidine carbonate. The amounts and the proportions employed are indicated below. As seen in Table II, the cream emulsion components each contained, prior to admixture, about 2.7 weight percent calcium hydroxide. Thus, the amounts of calcium hydroxide and of guanidine carbonate initially available for reaction in the two components employed for preparing an emulsion product of this invention were each at about half of that present in the two components of the commercial product.

Emulsion Product A—Regular Strength (A/R)

About 3.9 parts by weight cream emulsion component of Example 11 were mixed with 1 part by weight activator component containing about 11 weight percent of guanidine carbonate prior to admixture.

Emulsion Product A—Super Strength (A/S)

About 3.5 parts by weight cream emulsion component of Example 11 were mixed with 1 part by weight activator component containing about 11 weight percent of guanidine carbonate prior to admixture.

Emulsion Product B—Regular Strength (B/R)

About 4.4 parts by weight cream emulsion component of Example 10 were mixed with 1 part by weight activator component containing about 13 weight percent of guanidine carbonate prior to admixture.

Emulsion Product B—Super Strength (B/S)

About 3.6 parts by weight cream emulsion component of Example 10 were mixed with 1 part by weight activator component containing about 13 weight percent of guanidine carbonate prior to admixture.

Commercial Emulsion Product C—Regular Strength (C/R)

About 3.8 parts by weight cream emulsion component were mixed with 1 part by weight activator component.

Commercial Emulsion Product C—Super Strength (C/S)

About 3.5 parts by weight cream emulsion component were mixed with 1 part by weight activator component.

Tensile Strength Comparison

Procedure: The identical procedure was used in each procedure. A hair tress about 3.5 to about 4 inches long and about 0.2 weight of virgin (natural and previously untreated) human European natural brown hair (De Meo Brothers, New York) was given an 18 minute hair straightening treatment with a emulsion product A/R as follows. The emulsion product was applied to thoroughly coat the hair tress. The hair was smoothed with the back of a rattail comb at about 9 minutes and again at about 18 minutes of total treatment time. The emulsion product was then immediately removed from the treated hair tress by thorough water rinsing and then substantially immediately neutralizing any residual alkali remaining on the treated hair by shampooing with a commercial neutralizing conditioning shampoo. The commercial shampoo contained the polymeric hair conditioning agent, POLYQUATERNIUM-7.

Individual hair fibers (about 35) were then removed from the so treated hair tress. Each fiber was mounted at both of its ends (scalp end and tip end) onto vinyl tabs at a distance equal to about a 2-inch gage length. Each test hair fiber was soaked in deionized water for about 12 hours before measuring tensile strength. For measuring tensile strength, one tabbed end of an individual hair fiber was clamped to the crosshead of a Scott Tester Model CRE-500 and its opposite tabbed end was secured within a test cell filled with water so that the entire length of the fiber was maintained submerged in the water. Thus, the hair fiber remained water wet while load and elongation readings were taken.

The crosshead of the tester was set at a fixed speed of 2 inches/minute and the break force (tensile strength) or stress to break point of the tab-secured tress when extended under load elongation was measured. This procedure was repeated for each test fiber.

The change in tensile strength of the treated hair from that of similarly measured untreated hair control tresses was then calculated and the data analyzed statistically using the well known statistical t-test method to a 90 or 95% confidence level.

The foregoing procedure was repeated for each of the above emulsion products, A/S, B/R, B/S, and the Commercial emulsion products, C/R and C/S.

Result. The averaged data showed the tensile strength (TS) for the untreated and treated hair and the calculated % loss in TS for hair tresses following the use of each test emulsion product compared to the untreated hair control and was as follows:

EMULSION PRODUCT TREATMENT

| TS | None (Control) | A/R | A/S | B/R | B/S | C/R | C/S |
|---|---|---|---|---|---|---|---|
| avg. TS. | 76.05 | 53.68 | 42.7 | 55.27 | 45.97 | 38.39 | 37.76 |
| stan. dev. | 11.40 | 13.75 | 9.74 | 11.17 | 9.70 | 10.20 | 10.41 |
| % loss of TS. | 0 | 29.41 | 43.85 | 27.32 | 39.55 | 49.52 | 50.35 |

The data show surprisingly that hair tresses which were treated with the regular strength and the super strength emulsion products of this invention each retained significantly more tensile strength than that of hair tresses treated with the respective comparative regular strength and super strength commercial emulsion product. A loss in tensile strength of less than 30% is generally considered particularly desirable and both of the regular strength emulsion products of this invention, A/R and B/R, were within this range.

Substantially Complete Permanent Hair Straightening Efficacy Comparison

Procedure: The substantially permanent hair straightening efficacy of each one of the above emulsion products was determined and compared by the Intermittent Modulus Technique (IMT) described earlier. Clean hair fibers of virgin untreated African American hair (obtained from in-house salon subjects) preferably of a gauge length of about 1.5 centimeters (about 0.6 inches) were anchored at each end by a vinyl tab and then laterally positioned and aligned on the instrument balance beam and a constant load weight of about 0.5 grams was placed on the hair fiber.

A sufficient amount of selected emulsion product was applied to coat the test fiber. During the test procedure, an additional load weight of about 0.5 grams was applied to the fiber at intermittent intervals of about 30 seconds each. The supercontraction time (SCT) and the total relaxation treatment (TRT) time were thus determined. The total test period employed was about 30 minutes or until the SCT and the TRT were determined. Permanent hair straightening was judged as substantially complete if a SCT of 15 minutes or less and a TRT of less than about 25 minutes was obtained. This test procedure was repeated with each one of the above emulsion products, A/R, A/S, B/R, B/S, C/R and C/S.

The results were as follows:

EMULSION PRODUCT TREATMENT

| | A/R | A/S | B/R | B/S | C/R | C/S |
|---|---|---|---|---|---|---|
| SCT (Minutes) | 12 | 10 | 12 | 9 | 10 | 8.5 |
| TRT (Minutes) | 20 | 16.5 | 18 | 14 | is | 13 |

Results. The data show that the SCT and the TRT for each respective strength (R or S) of the emulsion products of this invention were substantially similar to one another. The SCT of the respective R or S strength was substantially comparable to that of comparative R and S strength of the commercial product. The TRT with the emulsion products of this invention was only slightly longer (i.e., slightly slower in speed) than the TRT of the commercial product but was well within a practical preferred time period. This data showed surprisingly that substantially complete permanent hair straightening was achieved in a practical treatment time with the emulsion products of this invention and that the hair straightening efficacy achieved was substantially equivalent to that of the commercial emulsion product.

Substantive Hair Conditioning Comparison

Procedure: The substantive conditioning efficacy of each of the above emulsion products was demonstrated by determining the binding of the cationic hair conditioning ingredient present in the emulsion product to the hair during the hair straightening step as follows.

A swatch (about 0.2 g) of virgin light blonde hair (De Meo Brothers, New York) was thoroughly washed with ethanol and dried. The dried hair swatch was then treated with a sufficient amount of selected emulsion product to coat the fiber and treated for about 3 minutes. The coated hair swatch was then rinsed with water, immediately shampooed with a commercial neutralizing shampoo containing no known cationic ingredient. Substantially immediately thereafter, while the washed hair was still damp, the hair was dipped into a 0.5% aqueous solution of a macromolecular polyanionic direct red azo dye, such as Pyrazol Fast Bordeaux 2BL (Sandoz) or Pyrazol Fast Red 7BSW, adjusted to about pH 3.5 with sulfuric acid for about 5 minutes at a temperature of about 40° C.

The hair swatch was then removed from the dye solution, rinsed well with water and visually examined for the presence and intensity of red (scarlet) coloration. The color intensity was rated on a numeric scale of 0 to 6, where a value of 0=no color and a value of 6=intense vivid scarlet red color. The test was carried out for each one of the above-identified emulsion products, identified as A/R, A/S, B/R, B/S, C/R and C/S.

It is known that the intensity of the red color visible on the hair swatch indicates the degree of deposition of cationic conditioning compound onto the hair. Absence of red color on the hair swatch indicates lack of substantivity of the cationic conditioning or compound. The intensity of the red color on the hair swatch, therefore, is a function of the extent of adsorption of the polyanionic dye, which in turn is a function of the cationic charge density on the hair, which again is a function of the extent of deposition and substantivity of the particular cationic compound on the hair.

This above test for cationic sorption by hair is well known in the art and is referred to commonly as the "Rubine Dye" test, because Rubine dye, 8 Direct Fast Red C.I. #32 (Erie Fast Rubine B Concentrate, now discontinued by its manufacturer Allied Chemical) was formerly used. See for example, Crawford, R. J. and Robbins, C. R., "A Replacement for Rubine Dye for Detecting Cationics on Keratin," *J. Soc. Cosm. Chem.*, 31, 273–278, (1980).

Result. The intensity of the scarlet red coloration imparted from the A/R and A/S emulsion products was scored at a value of 5.5 and from the B/R, B/S and the commercial emulsion product, C/R and C/S was scored a value of 5. The untreated control was scored at a value of 0. Thus, the data showed surprisingly that substantive conditioning was obtained with the emulsion products of this invention which were equal to or greater than that obtained with the commercial conditioning product.

These data demonstrate that the emulsion products of this invention were effective conditioning hair straightening emulsion products and further effectively lessened hair damage from the highly alkaline treatments.

For further comparison, the conditioning cream emulsion components of Examples 1, 2 and 3 were each separately directly applied, without admixing with any activator component, to naturally curly virgin African-American hair fibers and evaluated for permanent straightening efficacy by following the procedure of the IMT procedure above described. No straightening activity was observed over a total treatment time of about 30 minutes. These results also show surprisingly that the amount of strong caustic base present in the highly alkaline cream emulsions (pH about 11.7 to about 11.8) of about 2.5 weight percent calcium hydroxide and active lithium hydroxide ranging, respectively, from about 0.72, about 0.86 and about 1 weight percent, per se were unable to effect hair straightening in the absence of nitrogenous organic base.

EXAMPLE 17

This example illustrates the effect of increasing the calcium hydroxide content on the permanent hair straightening efficacy of an emulsion product of this invention prepared with the cream emulsion component of Example 1 and an activator component containing about 16.7 weight percent guanidine carbonate prior to admixture. The cream emulsion component of Example 1, as seen in Table I, contains about 1.25 weight percent lithium hydroxide and about 2.5 calcium hydroxide. For this comparison, the cream emulsion component of Example 1 was also prepared to contain about 2.75 and to contain about 3 weight percent in the cream emulsion component prior to admixture with the activator component.

Procedure: The hair straightening emulsion products indicated below in Table III were each prepared by admixing 1 part by weight of activator component with about 3.9 parts by weight of the indicated cream emulsion component to form a Regular strength (R) emulsion product and with about 3.6 parts by weight of the indicated cream emulsion product to form a Super strength (S) emulsion product. For comparison, a similar Regular strength and Super strength commercial no-lye type two component hair straightener product was employed. The commercial cream component contained, prior to admixture with activator component, about 6.26 weight percent calcium hydroxide and the activator component contained, prior to admixture with the cream component, about 28 weight percent guanidine carbonate.

Permanent hair straightening efficacy was determined by following the IMT procedure described in Example 16, except that a total test period of 15 minutes was employed.

TABLE III

| Emulsion Product | Cream Emulsion | Strength | No. Samples | SCT Min. | Standard Deviation |
|---|---|---|---|---|---|
| A | Example 1 | R | 10 | 6.33 | 0.61 |
| B | Example 1 | S | 8 | 6.97 | 0.44 |
| C | Example 1 with 2.75% Ca(OH)$_2$ | R | 8 | 7.19 | 0.65 |
| D | Example 1 with 2.75% Ca(OH)$_2$ | S | 8 | 6.66 | 0.74 |
| E | Example 1 with 3% Ca(OH)$_2$ | R | 5 | 7.95 | 0.46 |
| F | Example 1 with 3% Ca(OH)$_2$ | S | 9 | 8.56 | 0.68 |

TABLE III-continued

| Emulsion Product | Cream Emulsion | Strength | No. Samples | SCT Min. | Standard Deviation |
|---|---|---|---|---|---|
| G | Commercial | R | 6 | 7.58 | 0.73 |
| H | Commercial | S | 9 | 8.56 | 0.65 |

Result. Surprisingly, based on the SCT data obtained, the emulsion products of this invention, A–F, each achieved substantially complete permanent hair straightening within a total test time of about 15 minutes that was equivalent to or faster than that achieved with the commercial product, G–H. Surprisingly also, the SCT data obtained with the emulsion Products A–F show that the speed of relaxation tended to be slowed as the initial amount of calcium hydroxide was increased in the cream emulsion component of Example 1.

For further comparison, the hair straightening efficacy of the cream emulsion component F containing about 3 weight percent calcium hydroxide was applied directly to the hair without mixing with activator component and similarly tested. No SCT was noted indicating that no hair straightening activity occurred within the 15 minute total treatment time. This result indicates that the combination of about 3 weight percent calcium hydroxide and an active concentration of about 0.72 weight percent lithium hydroxide in the cream emulsion component per se, even though highly alkaline, was insufficient to effect hair relaxation.

EXAMPLE 18

This example compares the beneficial skin Sensation Irritation (SSI) ratings obtained when using conditioning hair straightening emulsion products of this invention compared to SSI ratings obtained with commercial conditioning no-lye type hair straighteners.

Procedure: In one salon study, a panel of 12 volunteer persons received a hair straightening treatment using a "half-head" comparison method. Each person received a hair straightening procedure on one side with a "Super" strength conditioning emulsion product prepared with about 3.5 parts by weight of the cream emulsion component of Example 11 and 1 part by weight of activator component containing about 11.5 weight percent guanidine carbonate, prior to admixture. The opposite side received a hair straightening procedure with the "Super" strength commercial conditioning hair straightener product (C/S) of Example 16 prepared as described in Example 16.

Each hair straightening procedure was immediately followed with the commercial conditioning neutralizing shampoo of Example 16. Hair conditioning was judged based on the tactile feel; i.e., smooth, soft, coated, or matted to the touch, of the wet hair immediately after shampooing. A smooth, soft feel is judged good hair conditioning. The average hair straightening process time period was determined by each person's hair type and on average ranged from about 14 to about 20 minutes.

Result. The overall hair straightening efficacy, conditioning of the wet relaxed hair and SSI ratings for both of the Super Strength emulsion products were each judged equivalent. Each Super strength emulsion product gave an SSI rating of 1 on 10 of 12 persons (about 84%) of the group; and an SSI rating of 2 on 1 person and an SSI rating of 3 on the remaining person, (each single person representing about 8% of the group). On one person, the degree of hair straightening obtained with the emulsion product of this invention was judged as being between textured (some curliness remaining) and substantially completely and permanently straightened (no curliness). Overall, however, the hair straightening effect obtained with an emulsion product of this invention was otherwise judged equivalent to that obtained with the commercial product in all respects.

The foregoing half-head testing procedure was repeated in a second salon test with a panel of 34 volunteer persons, except that the comparison was carried out using a "Regular" strength conditioning hair straightening product. The emulsion product was prepared by admixing about 3.9 parts by weight of the cream emulsion component of Example 11 with 1 part by weight of the above activator component. The emulsion product was applied to one side and was compared to the commercial "Regular" strength conditioning hair straightening emulsion product (C/R) of Example 16 prepared at "Regular" strength as described in Example 16 applied to the opposite side.

Result. Again, the overall hair straightening efficacy, wet combing conditioning of the wet hair and SSI ratings were each judged equivalent for both hair straighteners. The hair straightening emulsion product of this invention beneficially gave an SSI rating of 1 on 31 of 34 persons (about 91%) of the group and an SSI rating of 2 on the remaining 3 persons (about 9%) of the group. Surprisingly, these SSI ratings were slightly greater than those obtained with the commercial product, which gave SSI ratings of 1 on 30 of 34 persons (about 88%) of the group and SSI rating of 2 on the remaining 4 persons (12%) of the group.

The foregoing half-head testing procedure was repeated in a third salon test with a panel of 4 volunteer persons, except that the comparison was carried out using a "Mild" strength conditioning hair straightening product. The emulsion product was prepared with about 4.8 parts by weight of the cream emulsion component of Example 11 admixed with 1 part by weight of the above component activator. The emulsion product was applied to one side and was compared to commercial "Mild" strength conditioning emulsion product. The Mild strength commercial product was prepared by admixing 1 part by weight of the commercial activator component of Example 16 with about 4.8 parts by weight of the commercial cream component of Example 16.

Result. Again, the overall hair straightening efficacy, good wet combing conditioning of the wet hair and SSI ratings were each judged equivalent for both hair straighteners. Each of the Mild strength hair straightener emulsions gave an SSI rating of 1 on all 4 of the persons (100%) of the group.

These results demonstrate the effective hair straightening achieved with the conditioning hair straightening emulsion products of this invention within a practical treatment time of less than about 25 minutes. This result is surprising because the emulsion products of this invention initially employ less than about half the amounts of guanidine carbonate and calcium hydroxide usually employed in preparing the no-lye type hair straighteners of commerce. No undesirable discoloration of the hair, especially of naturally white gray hair, was noted with the emulsion products of this invention.

EXAMPLE 19

This example illustrates the straightening efficacy and beneficial SSI ratings obtained with straightener product prepared with the conditioning cream emulsion component of Example 1 (containing prior to admixture about 2.5 weight percent of calcium hydroxide and an active lithium hydroxide concentration of about 0.72 weight percent) and an activator component containing prior to admixture about 15 weight percent guanidine carbonate.

In a salon study, each member of a panel of 6 volunteer persons each initially having naturally curly hair received a hair straightening treatment. For 5 of the persons a "Super" strength emulsion product was employed and for 1 person a "Regular" strength emulsion product was employed. For use, 1 part by weight activator component was admixed with either about 3.6 parts by weight cream emulsion component to prepare a Regular strength emulsion product or about 4.4 parts by weight cream emulsion component to prepare a Super strength emulsion product. A commercial neutralizing conditioning shampoo was employed.

Within a total treatment time (inclusive of 8 minutes of application) of between less than about 12 to about 18 minutes, good permanent hair straightening was achieved with 50% of the group and a good degree of texturizing (i.e., most of the curliness permanently removed) was achieved with the remaining 50% of the group. An SSI rating of 1 was given to 5 of the 6 persons about (83%) of the group and an SSI rating of 2 was given to the remaining persons (17%) in the group. The amount of hair loss observed was judged normal.

In a second salon study the above procedure was repeated, except that the volunteer panel consisted of 37 persons each initially with naturally curly hair and the conditioning cream emulsion component of Example 6 (containing an active lithium hydroxide concentration of about 1 weight percent) was employed. Depending on the requirements of the individual person's hair, a Regular or Super strength emulsion product was prepared as described above and used.

The overall results showed that substantially complete permanent hair straightening was achieved with 31 persons (about 84%) of the group with good texturizing (partial permanent hair straightening) being achieved with the remaining 6 persons (about 16%) of the group within a total treatment time, inclusive of an 8 minute application time) in the time range of between about 15 to about 20 minutes. The amount of hair loss observed was judged normal (for a permanent hair straightening procedure).

SSI ratings of 1 were given on 25 of 37 persons (about 68%) of the group; SSI ratings of 2 were given on 4 persons (about 11%) of the group and SSI ratings of 3 were given on the remaining 8 persons (about 31%) of the group.

In a third salon study, the above procedure was repeated, except that the volunteer panel consisted of 7 persons each with naturally curly hair and the cream emulsion components of Examples 2, 8 or 9 (each of which prior to admixture contains about 2.5 weight percent calcium hydroxide and an active lithium hydroxide concentration of about 0.86 weight percent) was employed. The overall combined results showed that substantially complete permanent hair straightening was achieved with 5 persons (about 57%) of the group with good texturizing achieved with the remaining 3 persons (about 43%) of the group within a total treatment time, inclusive of an 8 minute application time) in the range of between about 13 to about 20 minutes. The amount of hair loss observed was judged normal.

SSI ratings of 1 were given on 5 of 7 persons (about 72%) of the group; an SSI rating of 2 was given on 1 person (about 14%) of the group and an SSI rating of 3 was given on the remaining person (about 14%) of the group.

The SSI ratings obtained were in the generally acceptable range but the number of SSI ratings of 1 given were less than were noted with the emulsion products in Example 19.

Based on the SSI ratings, the results indicated that when the sole conditioning agent was POLYQUATERNIUM-6 in the cream emulsion component, the amount of active lithium hydroxide present should preferably be less than about 1 weight percent, more preferably about 0.86 weight percent or less.

EXAMPLE 20

This example compares the substantially complete permanent hair straightening efficacy of conditioning emulsion products of this invention with that of commercial no-lye type hair straightening products following the IMT procedure of Example 16, except that each of the test emulsion products was prepared as described below.

Procedure: A series of emulsion products were separately prepared employing the cream emulsion components of Examples 10, 11, 12, 14, 15 and a modified version of the cream emulsion component of Example 11 (modified to contain about 19.75 weight percent petrolatum and also include about 0.01 weight percent aloe vera gel) (Ex. 11, mod.). The cream emulsion components were judged as being generally compositionally similar, since the non-caustic materials present have no known chemical hair straightening activity.

The various activator components employed, identified as a,b,c, or d, contained the following amounts of guanidine carbonate prior to admixture with cream emulsion component. The activator components, otherwise were compositionally similar to one another and to a commercial activator component, identified as (e) below.

| Activator | % Guanidine Carbonate |
|---|---|
| a | 10.5 |
| b | 12.5 |
| c | 11.2 |
| d | 11.7 |
| e | 28 (commercial product) |

The hair straightening emulsion products were prepared for use by admixing 1 part by weight (pbw) of indicated activator component with the indicated parts by weight (pbw) of cream emulsion component as shown below in Table IV. For further comparison, the straightening efficacy, if any, of the cream emulsion components of Examples 10, 11, 12, 14, 15 and Ex. 11 (Mod.) per se without being mixed with activator component were also tested.

As a control comparison, the commercial no-lye type conditioning hair straightening product of Example 16 (containing initially about 5.1 weight percent of calcium hydroxide) was also prepared as indicated. The commercial product thus constitutes a hair straightening emulsion product in which the sole strong chemical base is an organic base.

Permanent straightening efficacy was determined generally following the IMT procedure employing virgin untreated African American hair as described in Example 16, except that the straightening emulsion products were prepared with the combinations of activator components and cream emulsion components indicated below in Table IV.

TABLE IV

| Emulsion Product | Cream Emulsion | PBW Cream | 1 PBW Activator | SCT (min.) | TRT (min.) |
|---|---|---|---|---|---|
| A | Ex. 10 | 100 | None | 13 | 26.5 |
| B | Ex. 10 | 4 | a | 10 | 14.7 |
| C | Ex. 10 | 4 | b | 12 | 18 |
| D | Ex. 10 | 3.5 | b | 9 | 14 |
| E | Ex. 14 | 100 | None | 13.5 | 51 |
| F | Ex. 14 | 4 | c | None | — |
| G | Ex. 11 | 100 | None | 14 | 35 |
| H | Ex. 11 | 4 | c | 12 | 20.4 |
| I | Ex. 11 | 3.5 | c | 10 | 16.5 |
| J | Ex. 12 | 100 | None | 15 | 26.3 |
| K | Ex. 12 | 4 | c | 12 | 22.3 |
| L | Ex. 15 | 100 | None | 22 | — |
| M | Ex. 15 | 4 | c | None | — |
| N | Ex. 11(Mod.) | 10 | None | None | — |
| O | Ex. 11(Mod.) | 4.9 | d | None | — |
| P | Ex. 11(Mod.) | 4 | d | None | — |
| Q | Ex. 11(Mod.) | 3.6 | d | None | — |
| R | Ex. 11 | 4.9 | d | 12.5 | 24 |
| S | Ex. 11 | 4 | d | 11.3 | 21.3 |
| T | Ex. 11 | 3.6 | d | 11.3 | 18.7 |
| U | Commercial (note 1) | 4 | e | 10 | 15 |
| V | Commercial (Note 1) | 3.5 | e | 8.5 | 13 | note 1. The commercial cream emulsion contained about 5.1% calcium hydroxide.

Procedure: The permanent hair straightening efficacy of each one of the above emulsion products was determined and compared by the IMT procedure described in Example 16.

As described in Example 16, a sufficient amount of the selected emulsion product was applied to coat the test fiber and the supercontraction time (SCT) and the total relaxation treatment (TRT) time determined. The total test period lasted at least about 30 minutes or until the SCT and TRT was determined. If neither the SCT or the TRT was noted or determinable within about 1 hour, the test was ended. This test procedure was repeated with each one of the test emulsions. Permanent hair straightening was determined to be substantially complete if an SCT of 15 minutes or less and a TRT of 25 minutes or less was determined. A comparison of the substantially complete permanent hair straightening (CPS) obtained against the calculated theoretical amount of weight percent of alkali metal hydroxide, guanidine (calculated as free base), and calcium hydroxide initially present in each emulsion test is shown in Table V below.

TABLE V

| Test Emulsion | Calculated Initial Weight Percent | | | | | |
|---|---|---|---|---|---|---|
| | Alkali Metal Hydroxide (A) | Guanidine Base (B) | (A + B) | Calcium Hydroxide (C) | (A + B + C) | PS Y = Yes N = No |
| A | 1.03 | None | 1.03 | 2.7 | 3.73 | N |
| B | 0.82 | 1.31 | 2.2 | 2.16 | 4.36 | Y |
| C | 0.82 | 1.97 | 2.79 | 2.16 | 4.95 | Y |
| D | 0.8 | 1.97 | 2.77 | 2.11 | 4.88 | Y |
| E | 0.97 | None | 0.97 | None | 0.97 | N |
| F | 0.97 | 1.31 | 2.28 | None | 2.28 | N |
| G | 0.97 | None | 0.97 | 2.7 | 3.67 | N |
| H | 0.78 | 1.47 | 2.25 | 2.16 | 4.41 | Y |
| I | 0.76 | 1.67 | 2.43 | 2.11 | 4.54 | Y |
| J | 1.0 | None | 1.0 | 2.7 | 3.7 | N |
| K | 0.8 | 1.47 | 2.27 | 2.16 | 4.43 | Y |
| L | 1.0 | None | 1.0 | None | 1.0 | N |

TABLE V-continued

| Test Emulsion | Calculated Initial Weight Percent | | | | | PS Y = Yes N = No |
|---|---|---|---|---|---|---|
| | Alkali Metal Hydroxide (A) | Guanidine Base (B) | (A + B) | Calcium Hydroxide (C) | (A + B + C) | |
| M | 0.8 | 1.47 | 2.27 | None | 2.27 | N |
| N | None | None | — | 2.7 | 2.7 | N |
| O | None | 1.28 | 1.28 | 2.24 | 3.52 | N |
| P | None | 1.53 | 1.53 | 2.37 | 3.9 | N |
| Q | None | 1.66 | 1.66 | 2.57 | 4.23 | N |
| R | 0.8 | 1.28 | 2.08 | 2.24 | 4.32 | Y |
| S | 0.78 | 1.53 | 2.31 | 2.16 | 4.47 | Y |
| T | 0.76 | 1.66 | 2.42 | 2.11 | 4.53 | Y |
| U | None | 3.67 | 3.67 | 4.08 | 7.75 | Y (Control Regular) |
| V | None | 4.04 | 4.04 | 3.98 | 8.02 | Y (Control Super) |

The IMT data show that substantially complete hair straightening was achieved with the inventive B–D H, I, K, R, S and T test emulsion products prepared with the indicated cream emulsion component of Example 10, 11, 12, 14, 15 or Ex 11 (Mod) admixed with the indicated activator. In these test emulsion products, as seen in Table V, the combination of activator and cream emulsion represented about 0.76 to about 0.97 weight percent alkali metal hydroxide; about 1.28 to about 1.97 weight percent free organic base and initially about 2.11 to about 2.24 weight percent of calcium hydroxide.

When the sole strong chemical base present was calcium hydroxide, as in test emulsion N at about 2.7 weight percent, no hair straightening was observed, as expected.

When the sole strong chemical base was alkali metal hydroxide, as in test emulsions E (Lithium hydroxide) and n (sodium hydroxide), no hair straightening was observed. These results show that, at a concentration of less than 1 weight percent, lithium hydroxide (Test emulsion E) was insufficient to permanently straighten hair. Sodium hydroxide at a concentration of 1 weight percent in test emulsion also was insufficient to permanently straighten hair.

When the strong chemical base in the Test emulsion consisted of a combination of alkali metal hydroxide and calcium hydroxide as in test emulsions, A, G, and J incomplete permanent hair straightening took place. At most, some degree of hair texturizing was observed. This texturizing effect obtained with the test emulsions containing lithium hydroxide A, and G, was judged weak. The texturizing effect obtained with the test emulsion J, containing sodium hydroxide, was judged relatively good. This result suggested that the presence of the calcium hydroxide may have imparted some buffering of the high alkalinity of the sodium hydroxide.

When the sole strong chemical base was the organic base, as in Test emulsions O, P, and Q, no hair straightening (and no texturizing) was observed. In these test emulsions, the presence of the calcium ion did not appear to exert any activity.

When the sole strong chemical base was a combination of alkali metal hydroxide and organic base, as in test emulsions F and M, no hair straightening (or texturizing) was observed. Here again, the presence of the calcium ion did not appear to exert any activity.

The foregoing data demonstrate that each of the foregoing strong chemical bases; i.e., the nitrogenous organic base, the alkali metal hydroxide and the initial calcium hydroxide in the theoretical amounts present when the inventive emulsion is prepared are insufficient to produce hair straightening when each individual chemical base is the sole strong chemical base.

Thus, substantially complete permanent hair straightening was surprisingly achieved only with the inventive test emulsion products B, C, D, H, I, K, R, S and T in which the combination of the strong chemical bases was employed.

What is claimed is:

1. A highly alkaline emulsion for permanently straightening naturally curly hair on the scalp of a user through direct contact of said emulsion with said hair, said emulsion having an oil phase and an aqueous phase and containing a combination of three chemical bases one of which is a water-soluble nitrogenous organic base, a second of which is a water-soluble alkali metal hydroxide, and a third of which is a water-soluble alkaline earth metal hydroxide, said emulsion comprising:

(a) said nitrogenous organic base being present in said emulsion in an amount that is less than about 2 weight percent calculated as free organic base and based on total weight of said emulsion but said amount being insufficient to produce substantially complete permanent hair straightening in a hair contact time period of about 30 minutes when said nitrogenous organic base is used as the sole said chemical base in said emulsion, said nitrogenous organic base being characterized by having:
 (1) a $pK_a$ value of at least about 12, and
 (2) in its molecular structure a carbon atom that is:
  doubly bonded to a first nitrogen atom,
  singly bonded to a second nitrogen atom, and also,
  singly bonded to either another carbon atom or to a third nitrogen atom,
said nitrogenous organic base being selected from the group consisting of guanidines and acetamidines, (b) said alkali metal hydroxide being present in said emulsion in an amount that is less than about 1 weight percent calculated as hydroxide and based on total weight of said emulsion but said amount being insufficient to produce substantially complete permanent hair straightening in a hair contact time period of about 30 minutes when said alkali metal hydroxide is used as the sole said chemical base in said emulsion, and (c) said alkaline earth metal hydroxide being initially present as said emulsion is formed, said alkaline earth metal hydroxide being inoperative for the purpose of producing substantially complete permanent hair straightening in a hair contact time period of about 30 minutes when said alkaline earth metal hydroxide is used as the sole said chemical base in said emulsion, (d) lipophilic oleaginous material, (e) emulsifier, and (f) water, said emulsion having a pH in the range of about 11.5 to about 14 but containing respective amounts of each of said nitrogenous organic base, said alkali metal hydroxide and said alkaline earth metal hydroxide such that said emulsion produces a substantially complete permanent straightening of said user's hair when in contact therewith for a contact time period that is not longer than about 30 minutes.

2. The emulsion of claim 1 wherein on a 100 weight percent total emulsion basis:

(a) the quantity of said lipophilic oleaginous material is in the range of about 5 to about 60 weight percent, (b) the quantity of said emulsifier is in the range of about 0.01 to about 25 weight percent, and (c) the quantity of said water is in the range of about 35 to about 50 weight percent.

3. The emulsion of claim 1 wherein said nitrogenous organic base is produced in situ through hydrolysis of a dissolved, water-soluble salt of said nitrogenous organic base, said organic base salt being characterized by being hydrolyzed in water at 25° C., ambient pressure, and a pH value that is about equal to said $pK_a$ value.

4. The emulsion of claim 3 wherein said salt of said nitrogenous organic salt is guanidine carbonate in an amount of about 10 to about 20 weight percent based on total weight of said emulsion.

5. The emulsion of claim 3 wherein said emulsion is prepared by admixing together an activator component with a cream emulsion component, (a) said activator component comprises on a 100 weight percent total activator component basis:
about 10 to about 20 weight percent of said dissolved water-soluble salt of said nitrogenous organic base, and, correspondingly,
about 80 to about 90 weight percent of said water, and (b) said cream emulsion component comprises on a 100 weight percent total cream emulsion component basis:
about 0.6 to about 1.6 weight percent of said alkali metal hydroxide,
about 2 to about 3.5 weight percent of said alkaline earth metal hydroxide, and
about 5 to about 65 weight percent of said lipophilic oleaginous material,
about 0.01 to about 25 weight percent of said emulsifier, and
about 35 to about 60 weight percent of said water;
the relative proportions of each of said activator and said cream emulsion used in said admixing being such that said emulsion is produced.

6. The emulsion of claim 5 wherein based upon the total weight of the activator component and the cream emulsion component used in forming said emulsion:

(a) the quantity of said nitrogenous organic base that is present in said emulsion ranges from about 0.9 to about 2 weight calculated as free organic base, (b) the quantity of said alkali metal hydroxide that is present in said emulsion ranges from about 0.5 to about 1 weight percent calculated as hydroxide, and (c) the quantity of said alkaline earth metal hydroxide initially present ranges from about 1.5 to about 3 weight percent calculated as hydroxide.

7. The emulsion of claim 1 wherein on a 100 weight percent total emulsion basis:

(a) the quantity of said lipophilic oleaginous material is in the range of about 5 to about 60 weight percent, (b) the quantity of said emulsifier is in the range of about 0.01 to about 25 weight percent, and (c) the quantity of said water is in the range of about 35 to about 50 weight percent.

8. The emulsion of claim 1 wherein said nitrogenous organic base is produced in situ in the presence of said water-soluble alkaline earth metal hydroxide whereby there is further produced in situ a substantially water-insoluble dispersed alkaline earth metal salt having an anion that is derived from the anion of said water-soluble salt of said nitrogenous organic base.

9. The emulsion of claim 8 wherein the anion of said water-soluble salt of said nitrogenous organic base is selected from the group consisting of carbonate, sulfate, sulfite, phosphite, fluoride, oxalate, tartrate, laurate, stearate, alginate and mixtures thereof.

10. The emulsion of claim 1 wherein said alkaline earth metal comprises calcium.

11. The emulsion of claim 1 wherein said alkali metal is selected from the group consisting of lithium, sodium and potassium.

12. The emulsion of claim 11 wherein said alkali metal comprises lithium.

13. The emulsion of claim 1 wherein said lipophilic oleaginous material is selected from the group consisting of petrolatum, mineral oil, mineral jelly, lanolin, water-insoluble silicones, and mixtures thereof.

14. The emulsion of claim 1 which additionally contains a hair conditioning effective amount of a hair conditioner.

15. The emulsion of claim 14 wherein said hair conditioner is selected from the group consisting of water-dispersible monomeric quaternary ammonium compounds containing a long chain aliphatic group having from about 20 to about 24 carbon atoms inclusive and salts thereof, quaternary nitrogen containing polymers and salts thereof, and mixtures thereof.

16. The emulsion of claim 15 wherein hair conditioner is selected from the group consisting of behenyl trimethylammonium methosulfate, behenyl trimethylammonium chloride and mixtures thereof.

17. The emulsion of claim 1 wherein at least a component of each of said lipophilic oleaginous organic material and said emulsifier are each also present in said activator component.

18. The emulsion of claim 1 wherein said emulsifier comprises on a 100 weight percent total emulsion basis:

(a) about 2 to about 20 weight percent of a lipophilic nonionic emulsifier, and (b) about 0.01 to about 10 weight percent of a hydrophilic emulsifier.

19. The emulsion of claim 18 wherein said lipophilic nonionic emulsifier is selected from the group consisting of fatty alcohols derived from fatty acids containing about 12 to about 24 carbon atoms and adducts of said fatty alcohols with alkylene oxides containing at least two and less than four carbon atoms per starting alkylene oxide molecule, and mixtures thereof.

20. The emulsion of claim 18 wherein said hydrophilic emulsifier is selected from the group consisting of amphoteric surfactants, zwitterionic surfactants, nonionic surfactants, anionic surfactants and mixtures thereof.

21. A two component kit for preparing a highly alkaline emulsion useful for permanently straightening naturally curly hair, said kit comprising an activator component and a cream emulsion component, (a) said activator component comprising on a 100 weight percent total activator component basis:
about 10 to about 20 weight percent of a dissolved water-soluble salt of a water-soluble nitrogenous organic base, said nitrogenous organic base being characterized by having:
(1) a $pK_a$ value of at least about 12, and
(2) in its molecular structure a carbon atom that is:

doubly bonded to a first nitrogen atom,
singly bonded to a second nitrogen atom, and also,
singly bonded to either another carbon atom or to a third nitrogen atom,
said nitrogenous organic base being selected from the group consisting of guanidines and acetamidines, and, correspondingly,
about 80 to about 90 weight percent of water, and
(b) said cream emulsion component comprising on a 100 weight percent total emulsion cream component basis:
about 0.5 to about 1.6 weight percent of an alkali metal hydroxide,
about 2 to about 3.5 weight percent of an alkaline earth metal hydroxide, and
about 5 to about 65 weight percent of a lipophilic oleaginous material,
about 0.01 to about 25 weight percent of an emulsifier, and
about 35 to about 60 weight percent of water;
the amount of said activator component relative to the amount of said cream emulsion component in said kit being such that, when said activator component is admixed with said cream emulsion, said emulsion is produced.

22. The emulsion of claim 1 wherein said nitrogenous organic base is selected from the group consisting of
   a) guanidine;
   b) hydrated guanidine;
   c) guanidine substituted with 1–5 substituents selected from the group consisting of alkyl, carboxyalkyl, hydroxyalkyl, amino and alkylamino;
and mixtures thereof.

23. The emulsion of claim 22 wherein said nitrogenous organic base comprises guanidine, hydrated guanidine or mixtures thereof.

24. The emulsion of claim 1 wherein said nitrogenous organic base is selected from the group consisting of
   a) acetamidine;
   b) hydrated acetamidine;
   c) acetamidine substituted on the terminal carbon atom with a substituent selected from the group consisting of alkyl, amino and alkylamino;
and mixtures thereof.

25. The emulsion of claim 24 wherein said nitrogenous organic base comprises acetamidine.

26. The method of claim 1 wherein, in said emulsion, said alkali metal hydroxide comprises lithium hydroxide, said alkaline earth metal hydroxide comprises calcium hydroxide and said organic base comprises guanidine, hydrated guanidine and mixtures thereof.

* * * * *